US009993408B2

(12) United States Patent
Fevola et al.

(10) Patent No.: US 9,993,408 B2
(45) Date of Patent: Jun. 12, 2018

(54) COMPOSITIONS COMPRISING ZWITTERIONIC ALKYL-ALKANOYLAMIDES AND/OR ALKYL ALKANOATES

(71) Applicant: JOHNSON & JOHNSON CONSUMER INC., Skillman, NJ (US)

(72) Inventors: Michael J. Fevola, Belle Mead, NJ (US); Tobias J. Fuetterer, Princeton, NJ (US); Neil Warren Boaz, Kingsport, TN (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 43 days.

(21) Appl. No.: 14/856,830

(22) Filed: Sep. 17, 2015

(65) Prior Publication Data
US 2017/0079898 A1  Mar. 23, 2017

(51) Int. Cl.
C11D 1/00 (2006.01)
C11D 1/88 (2006.01)
C11D 1/94 (2006.01)
C11D 3/32 (2006.01)
A61K 8/46 (2006.01)
C11D 3/04 (2006.01)
C11D 1/66 (2006.01)
C11D 1/02 (2006.01)
A61Q 5/02 (2006.01)
A61Q 19/10 (2006.01)
A61K 8/44 (2006.01)

(52) U.S. Cl.
CPC ............ A61K 8/466 (2013.01); A61K 8/447 (2013.01); A61Q 5/02 (2013.01); A61Q 19/10 (2013.01); C11D 1/00 (2013.01); C11D 1/02 (2013.01); C11D 1/66 (2013.01); C11D 1/88 (2013.01); C11D 1/94 (2013.01); C11D 3/04 (2013.01); C11D 3/32 (2013.01); A61K 2800/30 (2013.01)

(58) Field of Classification Search
CPC .... C11D 1/00; C11D 1/02; C11D 1/66; C11D 1/88; C11D 1/94; C11D 3/04; C11D 3/32
USPC ............... 510/124, 126, 238, 422, 499, 501
See application file for complete search history.

(56) References Cited

U.S. PATENT DOCUMENTS

| 2,781,349 | A | | 2/1957 | Mannheimer | |
|---|---|---|---|---|---|
| 3,001,997 | A | | 9/1961 | Mannheimer | |
| 3,280,179 | A | | 10/1966 | Ernst | |
| 3,915,882 | A | * | 10/1975 | Nirschl | C11D 1/62 510/307 |
| 4,259,191 | A | | 3/1981 | Wagner | |
| 4,687,602 | A | | 8/1987 | Ballschuh et al. | |
| 4,879,204 | A | | 11/1989 | Ishigaki | |
| 5,696,070 | A | | 12/1997 | Tachizawa et al. | |
| 5,851,982 | A | | 12/1998 | Sakata et al. | |
| 5,876,705 | A | | 3/1999 | Uchiyama et al. | |
| 5,972,877 | A | | 10/1999 | Tsuda et al. | |
| 6,365,560 | B1 | * | 4/2002 | Chopra | A61K 8/31 510/141 |
| 7,335,627 | B1 | | 2/2008 | O'Lenick et al. | |
| 7,375,064 | B1 | | 5/2008 | O'Lenick, Jr. | |
| 7,507,399 | B1 | | 3/2009 | O'Lenick, Jr. | |
| 7,667,067 | B1 | | 2/2010 | Clendennen et al. | |
| 7,923,428 | B2 | | 4/2011 | Geffroy et al. | |
| 8,889,373 | B2 | | 11/2014 | Clendennen | |
| 8,900,625 | B2 | | 12/2014 | Damaj et al. | |
| 9,040,025 | B2 | | 5/2015 | Reierson et al. | |
| 9,120,846 | B2 | | 9/2015 | Haymore | |
| 9,533,951 | B2 | | 1/2017 | Boaz et al. | |
| 2004/0101505 | A1 | * | 5/2004 | Payne | A61K 8/416 424/70.31 |
| 2006/0035807 | A1 | * | 2/2006 | Kasturi | A61K 8/44 510/475 |
| 2007/0042030 | A1 | | 2/2007 | Cevc | |
| 2010/0016198 | A1 | * | 1/2010 | Bernhardt | C07C 303/06 510/127 |
| 2010/0159393 | A1 | | 6/2010 | Fiebag et al. | |
| 2011/0300093 | A1 | * | 12/2011 | Bendejacq | A61K 8/0291 424/70.16 |
| 2012/0040395 | A1 | | 2/2012 | Clendennen | |
| 2012/0277324 | A1 | | 11/2012 | Burk et al. | |
| 2014/0345483 | A1 | | 11/2014 | Imaizumi | |

(Continued)

FOREIGN PATENT DOCUMENTS

| CA | 2773738 C | 3/2011 |
|---|---|---|
| CN | 103468 A | 12/2013 |

(Continued)

OTHER PUBLICATIONS

English language Machine translation of EP205626.*
English language Machine translation of JP06184934.*
English language Machine translation of JP0730724.*
Wu et al., "Stereoisomers of N-substituted soft anticholinergics and their zwitterionic metabolite based on glycopyrrolate—syntheses and pharmacological evaluations", Die Pharmazie, Mar. 2008, 63(3): 200-209.
"Supplementary Examination Guidelines for Determining Compliance with 35 USC 112 and for Treatment of Related issues in patent Application", Fed Reg, vol. 76, No. 27, pp. 7162-7175 and slides 1, 64-67 (2011).

(Continued)

Primary Examiner — Gregory R Delcotto

(57) ABSTRACT

The present invention provides compositions utilizing a first zwitterionic ammonio-alkanamide and/or zwitterionic ammonio-alkanoate surfactant according to Formula 1 and an ingredient selected from the group consisting a surfactant other than the first zwitterionic surfactant, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliates, pH adjusters, inorganic salts, solvents, viscosity controlling agents and opacifying agents, wherein the composition is substantially free of alkylamidoamine and aminoalkylamine.

12 Claims, No Drawings

(56) References Cited

U.S. PATENT DOCUMENTS

| | | | |
|---|---|---|---|
| 2016/0271034 A1 | 9/2016 | Fevola et al. | |
| 2017/0022159 A1 | 1/2017 | Boaz et al. | |

FOREIGN PATENT DOCUMENTS

| | | | |
|---|---|---|---|
| CN | 103468228 | A | 12/2013 |
| DE | 1240872 | B | 5/1967 |
| DE | 2252687 | A1 | 5/1974 |
| DE | 274332 | A3 | 12/1989 |
| DE | 278053 | A1 | 4/1990 |
| DE | 278054 | A1 | 4/1990 |
| DE | 278061 | A1 | 4/1990 |
| EP | 0205626 | A1 | 12/1986 |
| EP | 2818930 | A1 | 12/2014 |
| JP | S4216415 | B1 | 9/1967 |
| JP | S4226523 | B1 | 12/1967 |
| JP | S56141375 | A | 11/1981 |
| JP | H06184934 | A | 7/1994 |
| JP | H07309724 | A | 11/1995 |
| JP | 1097065 | A | 4/1998 |
| WO | WO1998/033879 | A1 | 8/1998 |
| WO | WO2007/023336 | A2 | 3/2007 |
| WO | WO2007/059021 | A1 | 5/2007 |
| WO | WO2009/016375 | A2 | 2/2009 |
| WO | WO2009/136396 | A2 | 11/2009 |
| WO | WO2011/114876 | A1 | 9/2011 |
| WO | WO2011/146595 | A2 | 11/2011 |
| WO | WO2012/024233 | A2 | 2/2012 |
| WO | WO2012/061098 | A | 5/2012 |
| WO | WO2012/080018 | A2 | 6/2012 |
| WO | WO2012/148739 | A1 | 11/2012 |
| WO | WO2013/052087 | A1 | 4/2013 |
| WO | WO2016/064549 | A | 4/2016 |

OTHER PUBLICATIONS

Tastet et al, "Structure-efficiency relationships of zwitterionic detergents as protein solubilizers in two-dimensional electrophoresis", *Proteomics*, vol. 3, No. 2, Jan. 1, 20103 (XP003011172).

International search report dated Nov. 15, 2016, for international application PCT/US2016/050470.

Copending U.S. Appl. No. 15/170,097, filed Jun. 1, 2016, Michael J. Fevola et al.

ASTM 1173-07; Standard Test Method for Foaming Properties of Surface-Active Agents, (2007).

Chattopadhyay et al.; "Fluorimetric Determination of Critical Micelle Concentration Avoiding Interference from Detergent Charge"; Analytical Biochemistry, vol. 139, pp. 408-412 (1984).

Parris et al.; "Soap Based Detergent Formulation: XXIV. Sulfobetaine Derivatives of Fatty Amides[1,]"; Journal of the American Oil Chemists' Society, vol. 54, pp. 294-296 (1977).

Copending U.S. Appl. No. 14/518,476, filed Oct. 20, 2014, Michael J. Fevola et al.

Copending U.S. Appl. No. 14/518,505, filed Oct. 20, 2014, Neil Warren Boaz et al.

Copending U.S. Appl. No. 14/518,517, filed Oct. 20, 2014, Neil Warren Boaz et al.

Copending U.S. Appl. No. 14/856,656, filed Sep. 17, 2015, Neil Warren Boaz et al.

Abele et al., "Cationic and Zwitterionic Polymerizable Surfactants: Quaternary Ammonium Dialkyl Maleates. 1. Synthesis and Characterization", *Langmuir*, Feb. 1, 1999, 15(4):1033-1044.

Gandhi, "Applications of Lipase", *Journal of the American Oil Chemists' Society (JAOCS)*, Springer, DE, Jun. 1, 1997, 74(6):621-634.

Guo et al., "Synthesis of surface-functionalized, probe-containing, polymerized vesicles derived from ammonium bromide surfactants", *Langmuir*, Mar. 1, 1992, 8(3):815-823.

Hashmi et al., "Supramolecular Interaction Controlled Diffusion Mechanism and Improved Mechanical Behavior of Hybrid Hydrogel Systems of Zwitterions and CNT", *Macromolecules*, Dec. 21, 2012, 45(24):9804-9815.

Kratzer et al., "A Synethetic Route to Sulfobetaine Methacrylates with Varying Charge Distance", *European Journal of Organic Chemistry*, Dec. 5, 2014, 2014(36):8064-8071.

Liu et al., "Zwitterionic copolymer-based and hydrogen bonding-strengthened self-healing hydrogel", *RSC Advances: An International Journal to Further the Chemical Sciences*, Jan. 1, 2015, 5(42):33083-33088.

Spencer et al., "Zwitterionic Sulfobetaine Inhibitors of Squalene Synthase", *Journal of Organic Chemistry*, Jan. 1, 1999, 64(3):807-818.

Tremblay et al., "One-pot synthesis of polyunsaturated fatty acid amides with anti-proliferative properties", *Bioorganic & Medicinal Chemistry Letters*, Nov. 1, 2014, 24(24):5635-5638.

\* cited by examiner

COMPOSITIONS COMPRISING ZWITTERIONIC ALKYL-ALKANOYLAMIDES AND/OR ALKYL ALKANOATES

PARTIES TO JOINT RESEARCH AGREEMENT

Inventions described or claimed herein were made pursuant to a Joint Research Agreement between Eastman Chemical Company and Johnson & Johnson Consumer Inc.

FIELD OF INVENTION

The present invention relates to compositions comprising zwitterionic alkyl-alkanoylamide and/or alkyl alkanoate surfactants, as defined herein.

BACKGROUND OF THE INVENTION

Cleansing compositions are used to apply to the hair and/or skin of humans in order to provide cleansing of the respective part of the body to be cleaned. With respect to cleansing skin, cleansing formulations are designed to remove dirt, sweat, sebum, and oils from the skin, where cleansing is achieved through the use of conventional surfactants that aid in the uplifting of dirt and solubilization and removal of oily soils from the skin. In addition to removing unwanted materials from the skin, cleansing helps to promote normal exfoliation, and thereby rejuvenates the skin. Conventional detergents, such as cationic, anionic and nonionic surfactants, are widely used in a variety of cleansing compositions to impart such cleansing properties.

Also, certain zwitterionic surfactants, like betaines, sultaines and amphoacetates, are widely used in a variety of cleansing compositions. They are best known to generate desirable viscosity, foam and mildness in cleansing formulations, the most commonly used being cocamidopropyl betaine. Other examples include lauramidopropyl betaine, cocamidopropyl hydroxysultaine, lauramidopropyl hydroxysultaine, sodium lauroamphoacetate, sodium cocoamphoacetate, disodium cocoamphodipropionate and disodium lauroamphodipropionate, and the like. However, these zwitterionic surfactants all bear an alkylamidoamine moiety and recently have been recognized as possible allergens. In particular, cocamidopropyl betaine is now part of skin allergy screening tests. Further, allergens and skin irritants such as alkylamidoamines and aminoalkylamines are present as impurities in all of the zwitterionic surfactants noted above, the former an intermediate formed during the synthesis of the above zwitterionic surfactants and the latter an unreacted raw material used for the synthesis.

Applicants have recognized the desirability of developing cleansers that are substantially free of zwitterionic surfactants derived from alkylamidoamines and free of alkylamidoamine and aminoalkylamine impurities, while still fulfilling the demand for desirable viscosity, foam and mildness. Zwitterionic surfactants are best suited to help generate desirable viscosity, foam and mildness in cleansing formulations. Accordingly, applicants have recognized the need to develop cleansing compositions containing zwitterionic surfactants which do not contain an amidoamine moiety and that are substantially free of alkylamidoamines and aminoalkylamine impurities, and that exhibit desirable viscosity, foam and mildness for consumer use.

SUMMARY OF THE INVENTION

The present invention provides compositions comprising a first zwitterionic alkyl-alkanoylamide and/or alkyl alkanoate surfactant according to Formula 1, hereinafter referred to as "ZAA surfactants", and an ingredient selected from the group consisting of a second surfactant other than the first ZAA surfactant, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliants, pH adjusters, inorganic salts, solvents, viscosity controlling agents and opacifying agents, wherein the composition is substantially free of alkylamidoamine and aminoalkylamine.

DETAILED DESCRIPTION OF THE INVENTION

Applicants have discovered that compositions of the present invention overcome the disadvantages of the prior art and provide compositions that exhibit desirable viscosity and/or foaming action, as compared to the prior art, while maintaining excellent mildness to the skin and eyes. The compositions are substantially free of alkylamidoamine and aminoalkylamine impurities and substantially free of zwitterionic surfactants derived from an amidoamine-moiety. For example, as shown in the Examples, compositions comprising one or more ZAA surfactants tend to exhibit better viscosity building properties, similar or better foaming action, and at least comparable mildness (measured by EpiDerm™ and EpiOcular™ Test) compared to zwitterionic surfactants bearing an alkylamidoamine-moiety and/or containing alkylamidoamine and/or aminoalkylamine impurities, like cocamidopropyl betaine, sodium cocoamphoactetate and cocamidopropyl hydroxysultaine.

As used herein the term "zwitterionic alkyl-alkanoylamide and/or alkyl alkanoates", or "ZAA surfactants", refers to a zwitterionic surfactant according to Formula 1:

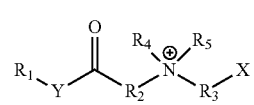

(Formula 1)

where $R_1$ is a linear, branched, saturated or unsaturated $C_6$ to $C_{22}$ alkyl hydrophobe;

$R_2$ is a linear, branched, or cyclic alkyl, hydroxyalkyl, or aromatic group;

$R_3$ is a linear or branched alkyl, hydroxyalkyl, or aromatic group;

$R_4$ is a linear or branched alkyl, hydroxyalkyl, or aromatic group;

$R_5$ is a linear or branched alkyl, hydroxyalkyl, or aromatic group; and any of $R_2$, $R_4$, or $R_5$ can by linked in a cyclic structure;

Y is O or NH; and

X is —$CO_2$—, —$SO_3$—, —$SO_4$—, —$PO_3H$—, or —$PO_4H$—.

The X-groups may or may not contain counterions $M^+$ or be protonated or deprotonated.

In certain embodiments, $R_2$ is a $C_1$-$C_8$ linear, branched, or cyclic alkyl, hydroxyalkyl, or aromatic group; $R_3$ is a $C_1$-$C_8$ linear or branched alkyl, hydroxyalkyl, or aromatic group; $R_4$ is a $C_1$-$C_8$ linear or branched alkyl, hydroxyalkyl, or aromatic group; and $R_5$ is a $C_1$-$C_8$ linear or branched alkyl, hydroxyalkyl, or aromatic group.

One specific example of a ZAA surfactant according to Formula 1 is 3-((4-(laurylamino)-4-oxobutyl)dimethylammonio)-2-hydroxypropane-1-sulfonate, shown in Formula 2:

(Formual 2)

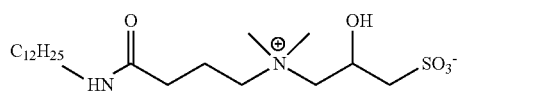

An example of a ZAA surfactant according to Formula 1 bearing an alkanoate group is 3-((2-(lauryloxy)-2-oxoethyl)dimethylammonio)-2-hydroxypropane-1-sulfonate, shown in Formula 2-2.

(Formula 2-2)

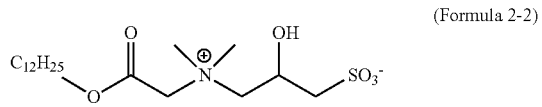

An example of a ZAA surfactant according to Formula 1 bearing an alkanoate group and a branched group is 3-((2-(lauryloxy)-2-oxo-1-methylethyl)dimethylammonio)-2-hydroxypropane-1-sulfonate, shown in Formula 2-3.

(Formula 2-3)

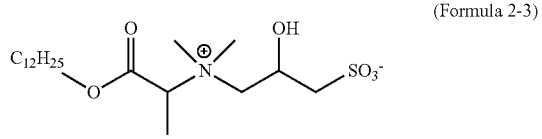

An example of a ZAA surfactant according to Formula 1 bearing a cyclic group is 3-(3-(laurylamino-oxomethyl)-1-methylpiperidinium)-2-hydroxypropane-1-sulfonate, shown in Formula 3, (Formula 3)

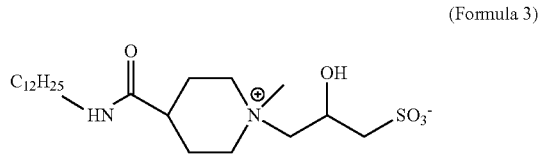

where $R_2$ and $R_4$ are linked in a cyclic structure, forming a piperidinium group.

Typically, compositions of the present invention will comprise from about 0.1% to about 30% w/w of ZAA surfactants, or from about 0.5% to about 15% w/w of ZAA surfactants, or from about 1% to about 10% w/w of ZAA surfactants, or from about 1.5% to about 7% w/w of ZAA surfactants, or about 1.5% to about 5% of ZAA surfactants, or about 1.5% to about 3.75% of ZAA surfactants, or about 2.25% to about 3.75% of ZAA surfactants.

As used herein the term "ZAA sulfonate surfactant" refers to a ZAA surfactant where X is —$SO_3$—, or any other protonated or salt form of the sulfonate group.

As used herein the term "ZAA sulfate surfactant" refers to a ZAA surfactant where X is —$SO_4$—, or any other protonated or salt form of the sulfate group.

As used herein the term "ZAA carboxylate surfactant" refers to a ZAA surfactant where X is —$CO_2$—, or any other protonated or salt form of the carboxy group.

As used herein the term "ZAA phosphate surfactant" refers to a ZAA surfactant where X is —$PO_4H$—, or any other protonated, ionized or salt form of the phosphate group.

As used herein the term "ZAA phosphonate surfactant" refers to a ZAA surfactant where X is —$PO_3H$—, or any other protonated, ionized or salt form of the phosphonate group.

Preferably, ZAA surfactants are free of alkylamidoamines and aminoalkylamines. They are the reaction products of alkyl amines or alkyl alcohols and amino acid derivatives. Thus, they do not contain alkylamidoamines (which are the reaction products of alkanoic acids and aminoalkylamines) or aminoalkylamines. The zwitterionic surfactants of the prior art are comprised of alkylamidoamines and aminoalkylamines and thus, contain such compounds.

The schematic process to make ZAA surfactants comprises:

(a) contacting an alcohol or amine or a mixture of alcohols or amines of Formula 4 with a dialkylamino-carboxylic acid or dialkylamino-carboxylic acid ester (amino acid derivative) or a mixture of dialkylamino-carboxylic acids or dialkylamino-carboxylic acid esters of Formula 5 in the presence of an enzyme at conditions effective to form an intermediate of Formula 6 (alkanoylamide or alkanoate), wherein Y, $R_1$, $R_2$, $R_4$, and $R_5$ are as defined above in Formula 1 and $R_7$ is hydrogen or $C_1$-$C_6$ alkyl; and (b) contacting the intermediate of Formula 6 with an alkylating agent at conditions effective to form the ZAA surfactant of Formula 1. Suitable alkylating agents are, for example, 2-chloro acetic acid or 2-hydroxy-3-chloro-propansulfonate or 1,3-propansultone.

In contrary, the schematic process to make zwitterionic surfactants of the prior art like e.g. Cocamidopropyl Betaine comprises:

(a*) contacting an alkanoic acid or a mixture of alkanoic acids of Formula 4* with an aminoalkylamine or a mixture of aminoalkylamines of Formula 5* at conditions effective to form an intermediate of Formula 6* (amidoamine); and (b*) contacting the intermediate of Formula 6* with an alkylating agent at conditions effective to form the zwitterionic surfactant like e.g. Cocamidopropyl Betaine.

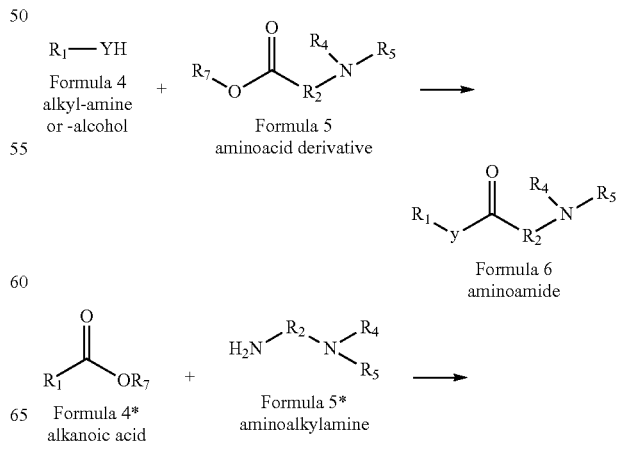

-continued

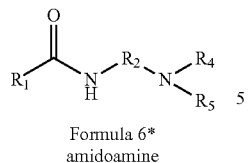

Formula 6*
amidoamine

All percentages listed in this specification are percentages by weight, unless otherwise specifically mentioned.

As used herein, the term "substantially free of alkylamidoamine and aminoalkylamine" means a composition that comprises alkylamidoamine and/or aminoalkylamine at maximum levels that mitigate or avoid the detrimental allergic or skin-irritating effects caused by alkylamidoamine and/or aminoalkylamine, for example, about 0.1% w/w or less, or about 0.1% w/w or less, or about 0.05% w/w or less, of alkylamidoamine and/or aminoalkylamine. Even more preferable, compositions are free of alkylamidoamine and aminoalkylamine.

Certain embodiments of the present invention may comprise a second surfactant other than ZAA surfactants. For example, compositions may further comprise anionic, cationic, non-ionic and/or zwitterionic surfactants in addition to the ZAA surfactants. In other embodiments, compositions may be substantially free of surfactants other than ZAA surfactants. As used herein, the term "substantially free of surfactant other than ZAA surfactants" means a composition that comprises less than 0.5%, or less than 0.1%, and more preferably less than 0.05% by weight of total surfactant other than ZAA surfactants. Even more preferable, compositions are free of surfactants other than ZAA surfactants. When an additional non-ZAA surfactant is used, the ratio of ZAA surfactant to non-ZAA surfactant (w/w) may be from about 0.003 to about 300, or about 0.1 to about 100, or about 0.1 to about 10, or about 0.1 to about 5, or about 0.3 to about 3.

Where applicable, chemicals are specified according to their INCI Name. Additional information, including definitions, suppliers, and trade names, can be found under the appropriate INCI monograph in the *International Cosmetic Ingredient Dictionary and Handbook, 14th Edition* published by the Personal Care Products Council, Washington D.C. Also available via the Personal Care Products Council On-Line INFOBASE (http://online.personalcarecouncl.org/jsp/Home.jsp)

As used herein, the term "anionic surfactant" refers to a surfactant molecule bearing at least a negative charge and no positive charge besides counterion(s), $M^+$. Suitable anionic surfactants include those selected from the following classes of surfactants:

Acyl isethionates

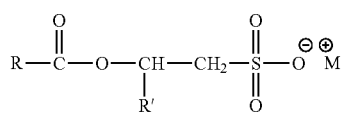

where $RCO=C_8$-$C_{20}$ acyl (linear or branched, saturated or unsaturated) or mixtures thereof, $R'=H$ or $CH_3$, $M^+$=monovalent cation, such as Sodium Cocoyl Isethionate (RCO=coco acyl, $R'=H$, $M^+=Na^+$) and Sodium Lauroyl Methyl Isethionate (RCO=lauroyl, $R'=CH_3$, $M^+=Na^+$).

Alkyl sulfosuccinates

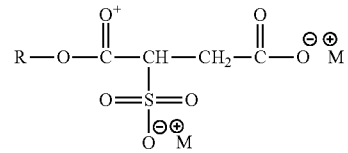

where $R=C_8$-$C_{20}$ alkyl (linear or branched, saturated or unsaturated) or mixtures thereof and $M^+$=monovalent cation, such as Disodium Lauryl Sulfosuccinate (R=lauryl, $M^+=Na^+$).

α-Sulfo fatty acid esters

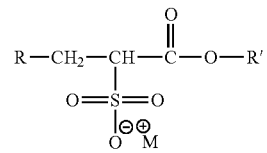

where $R=C_6$-$C_{16}$ alkyl (linear or branched, saturated or unsaturated) or mixtures thereof, $R'=C_1$-$C_2$ alkyl, and $M^+$=monovalent cation, such as Sodium Methyl 2-Sulfolaurate ($R=C_{10}H_{21}$, R'=methyl, $CH_3$, and $M^+=Na^+$);

α-Sulfo fatty acid salts

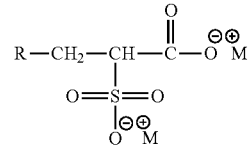

where $R=C_6$-$C_{16}$ alkyl (linear or branched, saturated or unsaturated) or mixtures thereof, $M^+$=monovalent cation, such as Disodium 2-Sulfolaurate ($R=C_{10}H_{21}$, $M^+=Na^+$);

Alkyl sulfoacetates

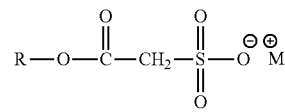

where $R=C_6$-$C_{18}$ alkyl (linear or branched, saturated or unsaturated) or mixtures thereof, $M^+$=monovalent cation, such as Sodium Lauryl Sulfoacetate (R=lauryl, $C_{12}H_{25}$, $M^+=Na^+$).

Alkyl sulfates

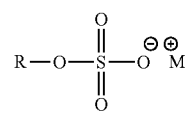

where $R=C_8$-$C_{20}$ alkyl (linear or branched, saturated or unsaturated) or mixtures thereof. Specific examples include TEA-Lauryl Sulfate (R=lauryl, $C_{12}H_{25}$, $M^+=$ HN(CH$_2$CH$_2$OH)$_3$), Sodium Lauryl Sulfate (R=lauryl, C$_{12}$H$_{25}$, M$^+$=Na$^+$), and Sodium Coco-Sulfate (R=coco alkyl, M$^+$=NO.

Alkyl glyceryl ether sulfonates or alkoxyl hydroxypropyl sulfonates:

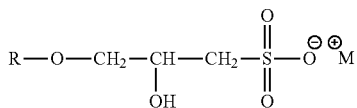

where R=C$_8$-C$_{24}$ alkyl (linear or branched, saturated or unsaturated) or mixtures thereof and M$^+$=monovalent cation, such as Sodium Cocoglyceryl Ether Sulfonate (R=coco alkyl, M$^+$=Na$^+$);

Alpha olefin sulfonates (AOS) prepared by sulfonation of long chain alpha olefins. Alpha olefin sulfonates consist of mixtures of alkene sulfonates,

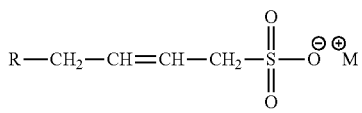

where R=C$_4$-C$_{18}$ alkyl or mixtures thereof and M$^+$=monovalent cation, and hydroxyalkyl sulfonates,

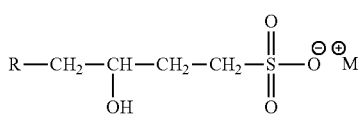

where R=C$_4$-C$_{18}$ alkyl or mixtures thereof and M$^+$=monovalent cation. Examples include Sodium C12-14 Olefin Sulfonate (R=C$_8$-C$_{10}$ alkyl, M$^+$=Na$^+$) and Sodium C14-16 Olefin Sulfonate (R=C$_{10}$-C$_{12}$ alkyl, M$^+$=Na$^+$);

Alkyl sulfonates or paraffin sulfonates:

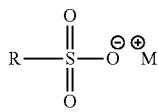

where R=C$_8$-C$_{24}$ alkyl (linear or branched, saturated or unsaturated) or mixtures thereof and M$^+$=monovalent cation. Examples include Sodium C13-17 Alkane Sulfonate (R=C$_{13}$-C$_{17}$ alkyl, M$^+$=Na$^+$) and Sodium C14-17 Alkyl Sec Sulfonate (R=C$_{14}$-C$_{17}$ alkyl, M$^+$=Na$^+$);

Alkylaryl sulfonates or linear alkyl benzene sulfonates

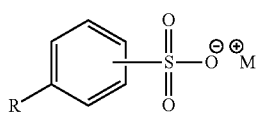

where R=C$_6$-C$_{18}$ alkyl (linear, saturated or unsaturated) or mixtures thereof and M$^+$=monovalent cation. Examples include Sodium Deceylbenzenesulfonate (R=C$_{10}$ alkyl, M$^+$=Na$^+$) and Ammonium Dodecylbenzensulfonate (R=C$_{12}$ alkyl, M$^+$=NH$_4^+$);

Alkyl ether sulfates

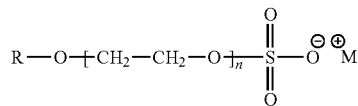

where R=C$_8$-C$_{24}$ alkyl (linear or branched, saturated or unsaturated) or mixtures thereof, n=1-12, and M$^+$=monovalent cation. Examples include Sodium Laureth Sulfate (R=C$_{12}$ alkyl, M$^+$=Na$^+$, n=1-3), Ammonium Laureth Sulfate (R=C$_{12}$ alkyl, M$^+$=NH$_4^+$, n=1-3), and Sodium Trideceth Sulfate (R=C$_{13}$ alkyl, M$^+$=Na$^+$, n=1-4);

Alkyl monoglyceride sulfates

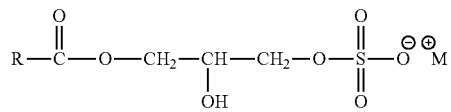

where RCO=C$_8$-C$_{24}$ acyl (linear or branched, saturated or unsaturated) or mixtures thereof and M$^+$=monovalent cation. Examples include Sodium Cocomonoglyceride Sulfate (RCO=coco acyl, M$^+$=Na$^+$) and Ammonium Cocomonoglyceride Sulfate (RCO=coco acyl, M$^+$=NH$_4^+$);

Alkyl ether carboxylates

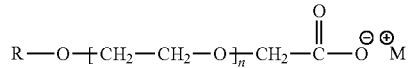

where R=C$_8$-C$_{24}$ alkyl (linear or branched, saturated or unsaturated) or mixtures thereof, n=1-20, and M$^+$=monovalent cation. Examples include Sodium Laureth-13 Carboxylate (R=C$_{12}$ alkyl, M$^+$=Na$^+$, n=13), and Sodium Laureth-3 Carboxylate (R=C$_{12}$ alkyl, M$^+$=Na$^+$, n=3);

Alkyl ether sulfosuccinates

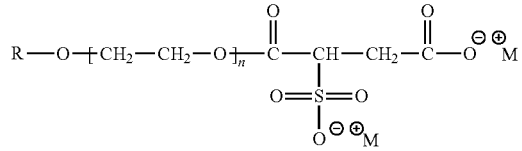

where R=C$_8$-C$_{20}$ alkyl (linear or branched, saturated or unsaturated) or mixtures thereof, n=1-12, and M$^+$=monovalent cation, such as Disodium Laureth Sulfosuccinate (R=lauryl, n=1-4, and M$^+$=Na$^+$)

Dialkyl sulfosuccinates

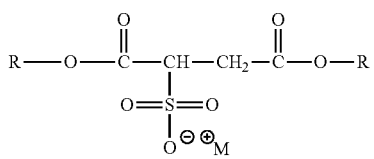

where R=$C_6$-$C_{20}$ alkyl (linear or branched, saturated or unsaturated) or mixtures thereof and $M^+$=monovalent cation, such as Diethylhexyl Sodium Sulfosuccinate (R=2-ethylhexyl, $M^+$=$Na^+$).

Alkylamidoalkyl sulfosuccinates

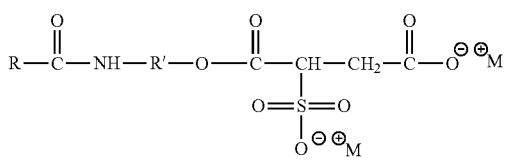

where R=$C_8$-$C_{20}$ alkyl (linear or branched, saturated or unsaturated) or mixtures thereof, R'=$C_2$-$C_4$ alkyl (linear or branched), and $M^+$=monovalent cation, such as Disodium Cocamido MIPA-Sulfosuccinate (RCO=coco acyl, R'=isopropyl, $M^+$=$Na^+$).

Alkyl sulfosuccinamates

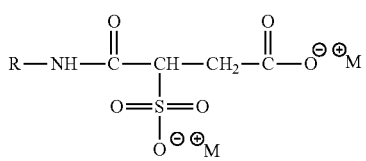

where R=$C_8$-$C_{20}$ alkyl (linear or branched, saturated or unsaturated) or mixtures thereof and $M^+$=monovalent cation, such as Disodium Stearyl Sulfosuccinamate (R=stearyl, $C_{18}H_{37}$, $M^+$=$Na^+$).

Acyl glutamates

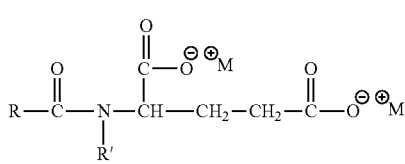

where RCO=$C_6$-$C_{20}$ acyl (linear or branched, saturated or unsaturated) or mixtures thereof, R'=H or $CH_3$, $M^+$=monovalent cation, such as Disodium Cocoyl Glutamate (RCO=coco acyl, R'=H, $M^+$=$Na^+$) and Disodium Lauroyl Glutamate (RCO=lauroyl, R'=H, $M^+$=$Na^+$).

Acyl aspartates

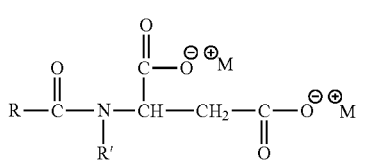

where RCO=$C_6$-$C_{20}$ acyl (linear or branched, saturated or unsaturated) or mixtures thereof, R'=H or $CH_3$, $M^+$=monovalent cation, such as Disodium N-Lauroyl Aspartate (RCO=lauroyl, R'=H, $M^+$=$Na^+$).

Acyl taurates

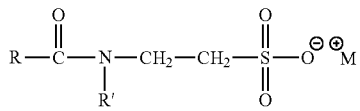

where RCO=$C_6$-$C_{20}$ acyl (linear or branched, saturated or unsaturated) or mixtures thereof, R'=H or $CH_3$, $M^+$=monovalent cation, such as Sodium Methyl Cocoyl Taurate (RCO=coco acyl, R'=$CH_3$, $M^+$=$Na^+$) and Sodium Cocoyl Taurate (RCO=lauroyl, R'=H, $M^+$=$Na^+$).

Acyl lactylates

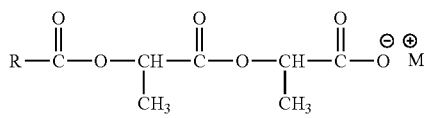

where RCO=$C_8$-$C_{20}$ acyl (linear or branched, saturated or unsaturated) or mixtures thereof, $M^+$=monovalent cation, such as Sodium Lauroyl Lactylate (RCO=lauroyl, $M^+$=$Na^+$).

Acyl glycinates and acyl sarcosinates

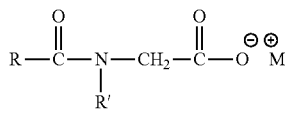

where RCO=$C_8$-$C_{20}$ acyl (linear or branched, saturated or unsaturated) or mixtures thereof, R'=H (glycinate) or $CH_3$ (sarcosinate), $M^+$=monovalent cation, such as Sodium Cocoyl Glycinate (RCO=coco acyl, R'=H, $M^+$=$Na^+$), Ammonium Cocoyl Sarcosinate (RCO=coco acyl, R'=$CH_3$, $M^+$=$NH_4^+$) and Sodium Lauroyl Sarcosinate (RCO=lauroyl, R'=$CH_3$, $M^+$=$Na^+$).

Anionic derivatives of alkyl polyglucosides, including: Sodium Lauryl Glucoside Carboxylate, Disodium Coco-Glucoside Citrate, Sodium Coco-Glucoside Tartrate, Disodium Coco-Glucoside Sulfosuccinate; Sodium Cocoglucosides Hydroxypropylsulfonate, Sodium Decylglucosides Hydroxypropylsulfonate, Sodium Laurylglucosides Hydroxypropylsulfonate; Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer; Anionic polymeric APG derivatives, such as those described in O'Lenick, U.S. Pat. Nos. 7,507,399; 7,375,064; and 7,335,627); and combinations of two or more thereof, and the like.

In certain embodiments, the compositions of the present invention are substantially free of anionic surfactants, and preferably are free of anionic surfactant.

As used herein, the term "sulfated anionic surfactant" refers to anionic surfactants containing a —$SO_4^-M^+$ group, with M+ being absent, or H+ or NH$_4^+$ or Na+ or K+ or other monovalent or multivalent anion. Examples of sulfated anionic surfactants include, but are not limited to, sodium lauryl sulfate and sodium laureth sulfate. In certain embodiments, the compositions of the present invention are substantially free of sulfated anionic surfactant, and preferably are free of sulfated anionic surfactant.

As used herein, the term "nonionic surfactant" refers to a surfactant molecule bearing no electrostatic charge. Any of a variety of nonionic surfactants is suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 sorbitan laurate and Polysorbate 20. PEG-80 sorbitan laurate is a sorbitan monoester of lauric acid ethoxylated with an average of about 80 moles of ethylene oxide. Polysorbate 20 is the laurate monoester of a mixture of sorbitol and sorbitol anhydrides condensed with approximately 20 moles of ethylene oxide.

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl glucosides comprise from about 1 to about 6 glucose residues per molecule of alkyl glucoside. A preferred glucoside is decyl glucoside, which is the condensation product of decyl alcohol with a glucose oligomer.

Another class of suitable nonionic surfactants includes "polyglycerol nonionic surfactant". Examples of polyglycerol nonionic surfactants include, but are not limited to, polyglycerol esters (PGEs), such as polyglycerol-10 laurate.

As used herein, the term "polyglyceryl nonionic surfactant" means an amphiphilic molecule comprising one or more nonionic hydrophilic segments comprised of a polyglyceryl moiety and one or more hydrophobic moieties. Examples of polyglyceryl nonionic surfactants include, but are not limited to, polyglyceryl esters (PGEs), such as polyglyceryl-10 laurate where PG=polyglyceryl moiety comprising ten (10) glyceryl repeat units, and R=C$_{11}$H$_{23}$:

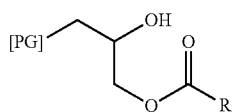

as well as, polyglyceryl-10 caprylate/caprate, polyglyceryl-10 cocoate, polyglyceryl-10 myristate, polyglyceryl-10 palmitate, polyglyceryl-10 oleate, polyglyceryl-12 laurate, and the like. PGEs of the present invention may include polyglyceryl moieties bearing multiple ester substitutions (i.e. the PGEs may be monoesters, diesters, triesters, etc.). Other polyglyceryl nonionic surfactants include polyglyceryl ethers, such as polyglyceryl-10 lauryl ether, where PG=polyglyceryl moiety comprising 10 glyceryl repeat units, and R=C$_{12}$H$_{25}$:

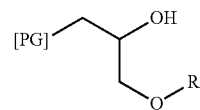

and the like. Still other polyglyceryl nonionic surfactants include polyglyceryl sorbitan fatty acid esters, such as polyglyceryl-20 sorbitan laurate, where PG=polyglycerol, the sum of all PG RUs=20, and R=C$_{11}$H$_{23}$. (see Bevinakatti, et al. WO 2009016375, assigned to Croda International PLC)

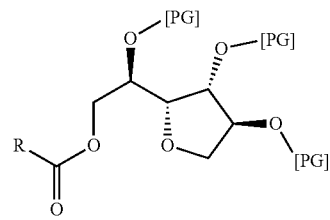

Any suitable polyglyceryl nonionic surfactants may be used in the compositions of the present invention. In certain preferred embodiments, the polyglyceryl nonionic surfactants are selected from the group consisting of polyglyceryl esters, polyglyceryl ethers, polyglyceryl sorbitan fatty acid esters, combinations of two or more thereof and the like. In certain more preferred embodiments, the polyglyceryl nonionic surfactants are selected from the group consisting of polyglyceryl esters, polyglyceryl ethers, and combinations of two or more thereof. In certain other preferred embodiments, the compositions of the present invention comprise one or more polyglyceryl nonionic surfactants selected from the group consisting of: polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate, and combinations of two or more thereof.

In preferred embodiments, the polyglyceryl nonionic surfactants used in the present invention have a total combined glyceryl degree of polymerization (DP) (i.e. total of all glyceryl repeat units in a given molecule) of from about 4 to about 40 repeat units. In certain more preferred embodiments, the polyglyceryl nonionic surfactants have a DP of from about 6 to about 30, more preferably from about 6 to about 20, more preferably, from about 6 to about 15, and more preferably from about 6 to about 12 glyceryl repeat units.

Any suitable amount of polyglyceryl nonionic surfactant may be used in the compositions of the present invention. In certain embodiments, the compositions comprise from greater than zero to about 25% by weight of polyglyceryl nonionic surfactant. In certain preferred embodiments, the compositions comprise from about 0.05 wt % to about 20 wt %, more preferably from about 0.1 wt % to about 15 wt %, and even more preferably from about 0.2 wt % to about 10 wt %, and still more preferably from about 0.25 wt % to about 5 wt % of total polyglyceryl nonionic surfactant.

Another class of suitable nonionic surfactants includes alkanolamides, like cocamide MEA and cocamide DEA.

As used herein, "zwitterionic surfactant other than a ZAA surfactant" refers to an amphiphilic molecule comprising a hydrophobic group and one or more hydrophilic groups comprising two moieties of opposite formal charges, or capable of bearing opposite formal charges (as a function of acid-base properties and solution pH). Sometimes such surfactants are also referred to as "amphoteric surfactants". Examples of zwitterionic surfactants other than a ZAA surfactant include:

Alkylamidoalkyl betaines of the formula:

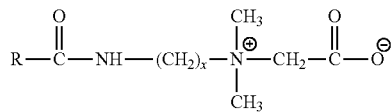

where RCO=$C_6$-$C_{24}$ acyl (saturated or unsaturated) or mixtures thereof and x=1-4. Examples include cocamidoethyl betaine (RCO=coco acyl, x=2), cocamidopropyl betaine (RCO=coco acyl, x=3), lauramidopropyl betaine (RCO=lauroyl, and x=3), myristamidopropyl betaine (RCO=myristoyl, and x=3), soyamidopropyl betaine (R=soy acyl, x=3), and oleamidopropyl betaine (RCO=oleoyl, and x=3).

Alkylamidoalkyl hydroxysultaines of the formula:

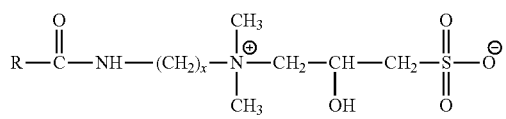

where RCO=$C_6$-$C_{24}$ acyl (saturated or unsaturated) or mixtures thereof. Examples include cocamidopropyl hydroxysultaine (RCO=coco acyl, x=3), lauramidopropyl hydroxysultaine (RCO=lauroyl, and x=3), myristamidopropyl hydroxysultaine (RCO=myristoyl, and x=3), and oleamidopropyl hydroxysultaine (RCO=oleoyl, and x=3).

Alkylamidoalkyl sultaines of the formula:

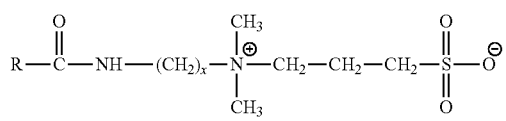

where RCO=$C_6$-$C_{24}$ acyl (saturated or unsaturated) or mixtures thereof. Examples include cocamidopropyl sultaine (RCO=coco acyl, x=3), lauramidopropyl sultaine (RCO=lauroyl, and x=3), myristamidopropyl sultaine (RCO=myristoyl, and x=3), soyamidopropyl betaine (RCO=soy acyl, x=3), and oleamidopropyl betaine (RCO=oleoyl, and x=3).

Amphoacetates of the formula:

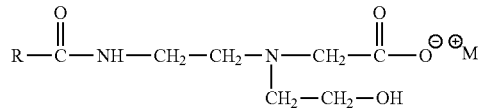

where RCO=$C_6$-$C_{24}$ acyl (saturated or unsaturated) or mixtures thereof and $M^+$=monovalent cation. Examples include sodium lauroamphoacetate (RCO=lauroyl and $M^+$=$Na^+$) and sodium cocoamphoacetate (RCO=coco acyl and $M^+$=$Na^+$).

Amphodiacetates of the formula:

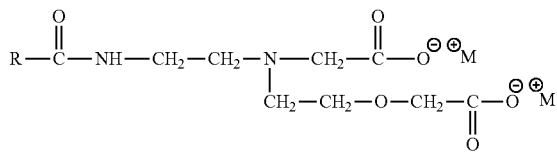

where RCO=$C_6$-$C_{24}$ acyl (saturated or unsaturated) or mixtures thereof and $M^+$=monovalent cation. Examples include disodium lauroamphodiacetate (RCO=lauroyl and M=$Na^+$) and disodium cocoamphodiacetate (RCO=coco acyl and M=$Na^+$).

Amphopropionates of the formula:

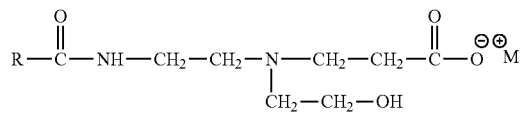

where RCO=$C_6$-$C_{24}$ acyl (saturated or unsaturated) or mixtures thereof and $M^+$=monovalent cation. Examples include sodium lauroamphopropionate (RCO=lauroyl and $M^+$=$Na^+$) and sodium cocoamphopropionate (RCO=coco acyl and $M^+$=$Na^+$).

Amphodipropionates of the formula:

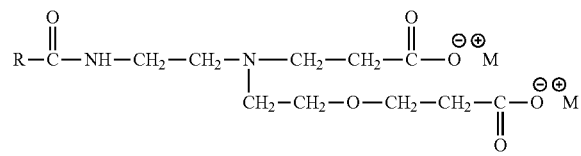

where RCO=$C_6$-$C_{24}$ acyl (saturated or unsaturated) or mixtures thereof and $M^+$=monovalent cation. Examples include disodium lauroamphodipropionate (RCO=lauroyl and $M^+$=$Na^+$) and disodium cocoamphodipropionate (RCO=coco acyl and $M^+$=$Na^+$).

Amphohydroxypropylsulfonates of the formula:

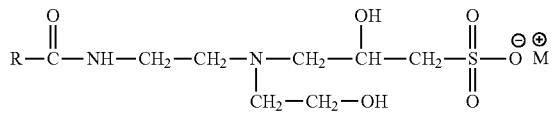

where RCO=$C_6$-$C_{24}$ acyl (saturated or unsaturated) or mixtures thereof and M$^+$=monovalent cation, such as sodium lauroamphohydroxypropylsulfonate (RCO=lauroyl and M$^+$=Na$^+$) and sodium cocoamphohydroxypropylsulfonate (RCO=coco acyl and M$^+$=Na$^+$).

Other examples include amphohydroxyalkylphosphates and alkylamidoalkyl amine oxides.

In certain embodiments of the present invention, the composition may further comprise an inorganic salt. Inorganic salts that are suitable for use in this invention include, but are not limited to, sodium chloride, potassium chloride, sodium bromide, potassium bromide, ammonium chloride, ammonium bromide and other mono-valent as well as multivalent ion containing salts. Typically, compositions of the present invention will comprise from about 0.05% to about 6% w/w of inorganic salt, or from about 0.1% to about 4% w/w of inorganic salt, or from about 0.1% to about 2% w/w of inorganic salt, or from about 0.1% to about 1.5% w/w of inorganic salt.

The pH of composition of the present invention is adjusted to preferably from about 3 to about 9, more preferably from about 3.5 to about 7, and most preferably from about 4 to about 6. The pH of the composition may be adjusted as low as 3 provided that formula stability and performance (e.g. foaming, mildness and viscosity) are not negatively affected. The pH of the composition may be adjusted to the appropriate acidic value using any cosmetically acceptable organic or inorganic acid, such as citric acid, acetic acid, glycolic acid, lactic acid, malic acid, tartaric acid, hydrochloric acid, combinations of two or more thereof or the like.

In certain embodiments of the present invention, the composition may further comprise a cationic surfactant. Classes of cationic surfactants that are suitable for use in this invention include, but are not limited to, alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred. In certain embodiments of the present invention, the composition comprises cationic conditioning polymers. Examples of suitable cationic conditioning polymers include cationic cellulose and its derivatives; cationic guar and its derivatives; and diallyldimethylammonium chloride. The cationic cellulose derivative may be a polymeric quaternary ammonium salt derived from the reaction of hydroxyethyl cellulose with a trimethylammonium substituted epoxide, known as Polyquaternium-10. The cationic guar derivative may be a guar hydroxypropyltrimonium chloride. Other useful cationic conditioning polymers are those derived from the monomer diallyldimethylammonium chloride. The homopolymer of this monomer is Polyquaternium-6. The copolymer of diallyldimethylammonium chloride with acrylamide is known as Polyquaternium-7. Other suitable conditioning polymers include those disclosed in U.S. Pat. No. 5,876,705, which is incorporated herein by reference.

The composition of this invention may further contain any other ingredients or additives typically used in personal care products, e.g., dermatological or in cosmetic formulations, including active ingredients. Examples of further ingredients or additives are surfactants, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliates, pH adjusters, solvents, viscosity controlling agents and opacifying agents, and the like, provided that they are physically and chemically compatible with the other components of the composition. Active ingredients may include, without limitation, anti-inflammatory agents, anti-bacterials, anti-fungals, anti-itching agents, moisturizing agents, plant extracts, vitamins, and the like. Also included are sunscreen actives which may be inorganic or organic in nature. Of particular interest are any active ingredients suited for topical application of personal care compositions.

Examples of thickeners and rheology modifiers, include but are not limited to, naturally-derived polysaccharides including xanthan gum, dehydroxanthan gum, *Cyamopsis tetragonoloba* (guar) gum, *cassia* gum, *Chondrus crispus* (carrageenan) gum, alginic acid and alginate gums (e.g. algin, calcium alginate, etc.), gellan gum, pectin, microcrystalline cellulose, nonethoxylated derivatives of cellulose (e.g. sodium carboxymethylcellulose, hydroxypropyl methylcellulose, etc.), and hydroxypropyl guar, and synthetic polymers such as, acrylic alkali-swellable emulsion (ASE) polymers, such as Acrylates Copolymer, available under the trade name Carbopol® AQUA SF-1 from Lubrizol Corp., Brecksville, Ohio, hydrophobically-modified acrylate crosspolymers, such as Acrylates C10-30 Alkyl Acrylates Crosspolymer, available under the trade name Carbopol® 1382 from Lubrizol Corp., Brecksville, Ohio, as well as micellar thickeners, such as: cocamide MIPA, lauryl lactyl lactate, or sorbitan sesquicaprylate, and combinations of two or more thereof and the like;

Examples of preservatives and preservative boosters include but are not limited to organic acids (like e.g. benzoic acid, lactic acid, salicylic acid), benzyl alcohol, caprylyl glycol, decylene glycol, ethylhexylglycerin, gluconolactone, methylisothazolinone, and combinations of two or more thereof, and the like.

The following examples are meant to illustrate the present invention, not to limit it thereto.

EXAMPLES

Test methods used in the Examples are described as follows:
Zero-Shear Viscosity Test:

Determinations of zero-shear apparent viscosity of the cleansing compositions were conducted on a controlled-stress rheometer (AR-2000™, TA Instruments Ltd., New Castle, Del., USA). Steady-state shear stress sweeps were performed at 25.0±0.1° C. using a cone-plate geometry. Data acquisition and analysis were performed with the Rheology Advantage software v4.1.10 (TA Instruments Ltd., New Castle, Del., USA). Zero-shear apparent viscosities for Newtonian fluids are reported as the average of viscosity values obtained over a range of shear stresses (0.02-1.0 Pa). For pseudoplastic (shear-thinning) fluids, zero-shear apparent viscosities were calculated via the fitting of shear stress sweep data to an Ellis viscosity model. Except otherwise stated, viscosities are given in centiPoise (cps).
Formulation Foam Test:

The following Formulation Foam Test was performed on various cleansing compositions to determine the foam volume upon agitation according to the present invention. First, a solution of the test composition is prepared in simulated tap water. To represent the hardness of tap water, 0.455 g of calcium chloride dihydrate (Sigma-Aldrich) is dissolved per 1000 g of DI water, and mixed for 15 minutes prior to use Depending upon the appropriate level required to provide the appropriate level of foam for the instrument to measure, one (1.0) or five (5.0) grams of test composition is weighed, and this solution is added to 1000 g and mixed until homogeneous for 15 minutes prior to use. To determine the Formulation Foam Volume, the test composition (1000 mL) was added to the sample tank of a SITA™ R-2000 foam tester (commercially available from Future Digital Scientific, Co.; Bethpage, N.Y.). The test parameters were set to repeat three runs (series count=3) of 250 ml sample size (fill volume=250 ml) with thirteen stir cycles (stir count=13) for a 15 second stir time per cycle (stir time=15 seconds) with the rotor spinning at 1200 RPM (revolution=1200) at a temperature setting of 30° C.±2° C. Foam volume data was collected at the end of each stir cycle and the average and standard deviation of the three runs was determined. The Maximum Foam Volume was reported for each Example as the value after the thirteenth stir cycle.

EpiDerm™ Skin Model with Cytotoxicity and Cytokine Endpoints:

Upon receipt of the EpiDerm™ Skin Kit (MatTek Corporation), the solutions were stored as indicated by the manufacturer. The EpiDerm™ tissues were stored at 2-8° C. until use. The day before dosing, an appropriate volume of EpiDerm™ hydrocortisone free-assay medium (prepared without hydrocortisone) (HCF-AM) will be removed and warmed to approximately 37° C. Nine-tenths (0.9) mL of HCF-AM will be aliquoted into the wells of 6-well plates. Each EpiDerm™ will be inspected for air bubbles between the agarose gel and tissue insert prior to opening the sealed package. Tissues with air bubbles greater than 50% of the tissue insert area will not be used. The 24-well shipping containers will be removed from the plastic bag and the surface disinfected with 70% ethanol. An appropriate number of EpiDerm™ tissues will be transferred aseptically from the 24-well shipping containers into the 6-well plates for the test articles and the negative control conducted in parallel to the test article exposures. The EpiDerm™ tissues will be incubated at 37±1° C. in a humidified atmosphere of 5±1% $CO_2$ in air (standard culture conditions) over-night (at least 16 hours), to acclimate the tissue and stabilize cytokine expression. Upon opening the bag, any unused tissues remaining on the shipping agar at the time of tissue transfer will be briefly gassed with an atmosphere of 5% $CO_2$/95% air, and the bag will be sealed and stored at 2-8° C. for subsequent use.

MTT Assay: At least 16 hours after initiating the tissues, the medium will be removed from under the tissue and 0.9 mL of fresh, pre-warmed HCF-AM will be added to each well. Each test article, and the negative control (for the test article exposures), will be tested by treating three EpiDerm™ tissue constructs for the exposure time specified in Protocol Attachment 1. One hundred microliters (100 μL) of the liquid test article (and negative control) or 30±1 mg (solid test articles) will be applied to each EpiDerm™. At the end of the test article exposure period, each tissue will be rinsed five times with approximately 0.5 mL per rinse of $Ca_{++}$ and $Mg_{++}$ Free Dulbecco's Phosphate Buffered Saline ($Ca_{++}Mg_{++}$Free-DPBS). The DPBS will be gently pipetted into the well and then drawn off with an aspirator. Care must be exercised to avoid touching the surface of the tissue. After rinsing, each tissue will be placed in the designated well of a new 6-well plate containing 0.9 mL of fresh HCF-AM. Once rinsed, the tissues will be returned to the incubator and incubated at standard culture conditions for the post-exposure incubation period. Positive/negative control: The positive control, 100 μL of 1% Triton®-X-100, will be tested in duplicate tissues for 4 and 8 hours cultured using standard Assay Media containing hydrocortisone. The tissues will be incubated under standard culture conditions for the appropriate exposure times. One hundred μL of sterile water will be used to dose the negative control conducted in parallel. Duplicate tissues will be treated with the negative control for the 8 hour exposure time cultured in standard Assay Media containing hydrocortisone. The negative control conducted in parallel to the test article exposures will be tested in triplicate tissues in hydrocortisone-free Assay Media. A 10× stock of MTT prepared in PBS (filtered at time of batch preparation) will be thawed and diluted in warm MTT Addition Medium to produce the 1.0 mg/mL solution no more than two hours before use. Three hundred μL of the MTT solution will be added to each well of a prelabelled 24-well plate. After the appropriate exposure time, the 6-well plate will be gently agitated to evenly mix any cytokine released into the medium. The positive control-treated tissues and associated negative control will be rinsed to remove the control articles. Each EpiDerm™ will be removed from the incubation medium, rinsed with $Ca_{++}$ and $Mg_{++}$ Free Dulbecco's Phosphate Buffered Saline ($Ca_{++}Mg_{++}$Free-DPBS) to remove the test article, and the excess $Ca_{++}Mg_{++}$Free-DPBS will be decanted. The EpiDerm™ tissues will be transferred to the appropriate wells after rinsing. The test article and associated negative control-treated tissues will be blotted dry (not rinsed) before transfer into the MTT solution. The 24-well plates will be incubated under standard culture conditions for 3±0.1 hours. The medium under each EpiDerm™ tissues treated with each test article, negative and positive control, respectively, will be repeatedly pipetted up and down to evenly distribute the cytokines, will be removed and placed evenly into two to three prelabeled cryovials. The vials will be quick-frozen in a dry ice/ethanol bath and stored at ≤60° C. for subsequent cytokine analysis. After the 3-hour incubation in MTT, the EpiDerm™ tissues will be blotted on absorbent paper and transferred to a prelabelled 24-well plate containing 2.0 mL of isopropanol in each well. The plates will be covered with parafilm and stored refrigerated until the last samples are harvested. If necessary, plates may be stored overnight (or up to 24 hours after the tissue is harvested) in the refrigerator prior to extracting the MTT. Then the plates will be shaken for approximately 2 hours at room temperature. At the end of the extraction period, the liquid within the tissue inserts will be decanted into the well from which the tissue inserts was taken. The extract solution will be mixed and 200 μL transferred to the appropriate wells of the 96-well plates. Two hundred μL of isopropanol will be added to the wells designated as blanks. The absorbance at 550 nm ($OD_{550}$) of each well will be measured with a Molecular Devices Vmax plate reader. The mean $OD_{550}$ value of the blank wells will be calculated. The corrected mean $OD_{550}$ value of the negative control(s) will be determined by subtracting the mean $OD_{550}$ value of the blank wells from their mean $OD_{550}$ values. The corrected $OD_{550}$ values of the individual test article exposure times and the positive control exposure times will be determined by subtracting from each the mean $OD_{550}$ value for the blank wells. All calculations will be performed using an Excel spreadsheet.

Corr. test article exposure time $OD_{550}$=Test article exposure time $OD_{550}$−Blank mean $OD_{550}$ If killed controls (KC) are used, the following additional calculations will be performed to correct for the amount of MTT reduced directly by test article residues. The $OD_{550}$ value for the negative control killed control will be subtracted from the $OD_{550}$ values for each of the test article-treated killed controls (at each appropriate exposure time), to determine the net $OD_{550}$ values of the test article-treated killed controls.

Net $OD_{550}$ for each test article KC=Raw $OD_{550}$ test article KC−Raw $OD_{550}$ negative control KC The net $OD_{550}$ values represent the amount of reduced MTT due to direct reduction by test article residues at specific exposure times. In general, if the net $OD_{550}$ value is greater than 0.150, the net amount of MTT reduction will be subtracted from the corrected $OD_{550}$ values of the viable treated tissues, at each corresponding exposure time, to obtain a final corrected $OD_{550}$ value. These final corrected $OD_{550}$ values will then be used to determine the % of Control viabilities at each exposure time.

Final Corrected $OD_{550}$=Corrected test article $OD_{550}$ (viable)−Net $OD_{550}$ test article (KC)

Finally, the following % of Control calculations will be made:

$$\% \text{ Viability} = \frac{\text{Final corrected } OD_{550} \text{ of Test Article or Positive Control}}{\text{corrected mean } OD_{550} \text{ of Negative Control}} \times 100$$

An exposure time response curves will be plotted, for the positive control, with the % of control on the ordinate and the positive control exposure time on the abscissa. The $ET_{50}$ will be interpolated from the plot.

IL-1α Immunoassay: Microtiter plates coated with monoclonal anti-IL-1 α will be stored at 2-8° C. until time of use. All other reagents will be stored as described in the instructions provided with the kit. The diluent RD5-5 will be used to prepare the standard or any supernatant dilutions. A 250 pg/mL IL-1 α standard will be prepared by diluting the stock vial with 5 mL of RD5-5, which will sit for at least 15 minutes prior to use. A series of IL-1 α standards will be prepared from the 250 pg/mL stock ranging from 250 pg/mL to 3.9 pg/mL. The standard series will be prepared by adding 500 μL of the 250 pg/mL stock to 500 μL of diluent RD5-5 (making 125 pg/mL) and then making a series of five more dilutions (dilution factor of 2). Diluent RD5-5 is used as the zero standard. The standard series will be prepared in duplicate. Dilutions may be performed on the samples to keep values within the linear range of the assay. Generally, dilutions shall be performed in RD5-5 buffer or assay media as appropriate. Data will be expressed in terms of the concentration in the original sample. All reagents and samples should be at room temperature for testing. Prior to addition of the samples or standards, 50 μL of Assay Diluent RD1-83 (mixed well before use) will be added to each well. Two hundred μL standards or sample (represented by the medium collected from the tissues treated with test article) will be added to the appropriate antibody-coated wells. The wells will be covered with adhesive strip and incubated at room temperature for 2 hours. After incubating the plate for 2 hours at room temperature, the solutions will be removed from the wells and the plate washed three times with approximately 250 μL of wash solution. It is important to completely remove the liquid from each well at the end of each rinse. Two hundred μL of enzyme conjugate (IL-1 α Conjugate) will then be added to all wells, the wells covered with a new adhesive strip, and the plate will be incubated in the dark for 1 hour at room temperature. After this incubation, the solutions will be removed from the wells and the plate washed three times with approximately 250 μL of wash solution. Again, it is important to completely remove the liquid from each well at the end of each rinse. Two hundred μL of chromogenic substrate (Substrate Solution) will be added to each well. The plate will be incubated for 20 minutes at room temperature, protected from light, without shaking. Fifty μL of stop solution will be added to all the wells to stop the reaction. The plate will be read at 450 nm, subtracting the absorbance at 540 or 570 nm, within 30 minutes of stopping the reaction ($OD_{450-570}$). The $OD_{450-570}$ of each test sample and IL-1 α standard will be determined. The corrected $OD_{450-570}$ for the test samples and each IL-1 α standard will be determined by subtracting the mean $OD_{450-570}$ of the blank wells. The average of the corrected $OD_{450-570}$ for each IL-1 α standard will be calculated and will be used to generate the standard curve. The standard curve will be plotted as the concentration of the standards (y-axis) versus the corresponding corrected average absorbance (x-axis). The amount of IL-1 α released by the test sample groups (controls and test articles as appropriate) will be mathematically interpolated from the standard curve (quadratic).

EpiOcular™ Test:

Upon receipt of the EpiOcular™ Human Cell Construct Kit (MatTek Corporation), the solutions were stored as indicated by the manufacturer. The EpiOcular™ human cell constructs were stored at 2-8° C. until used. On the day of dosing, EpiOcular™ Assay Medium was warmed to approximately 37° C. Nine-tenths mL of Assay Medium were aliquoted into the appropriate wells of 6-well plates. The six-well plates were labeled to indicate test article and exposure time. The constructs were inspected for air bubbles between the agarose gel and cell culture insert prior to opening the sealed package. Cultures with air bubbles covering greater than 50% of the cell culture area were not used. The 24-well shipping containers were removed from the plastic bag and their surfaces were disinfected with 70% ethanol. The EpiOcular™ human cell constructs were transferred aseptically into the 6-well plates. The constructs were then incubated at 37±1° C. in a humidified atmosphere of 5±1% $CO_2$ in air (standard culture conditions) for at least one hour. The medium was then aspirated and 0.9 mL of fresh Assay Medium were added to each assay well below the EpiOcular™ human cell construct. The plates were returned to the incubator until treatment was initiated.

The test articles were administered to the test system as 3% w/v dilutions in sterile, deionized water (positive and negative control, 1.0% Triton®-X-100 and Johnson's Baby Shampoo, respectively, were administered to the test system as 10% w/v dilutions in sterile, deionized water). Each test article dilution was prepared by weighing the test article into a prelabeled conical tube. Sterile, deionized water was added until a 3% w/v or 10% w/v dilution was achieved and the tube was vortexed prior to application. For the remainder of this report, each test article dilution is referred to as the test article.

The EpiOcular™ cultures were treated in duplicate with the test articles at specific exposure times (from 0.33 up to 16 hours, four time points each). One hundred microliters of each test article were applied to each EpiOcular™ human cell construct. Duplicate cultures of the negative control (exposure time control), 100 μL of sterile, deionized water (Quality Biological), were exposed for 0.25, 4, 8, and 24 hours. Duplicate cultures of the positive control, 100 μL of 0.3% Triton®-X-100 (Fisher), were exposed for 15 and 45 minutes. The exposed cultures were then incubated for the appropriate amount of time at standard culture conditions. After the appropriate exposure time, the EpiOcular™ cultures were extensively rinsed with Calcium and Magnesium-Free Dulbecco's Phosphate Buffered Saline ($Ca_{++}Mg_{++}$ Free-DPBS) and the wash medium was decanted. After rinsing, the tissue was transferred to 5 mL of Assay Medium for a 10 to 20 minute soak at room temperature to remove any test article absorbed into the tissue. A 1.0 mg/mL solution of MTT in warm MTT Addition Medium was prepared no more than 2 hours before use. Three-tenths mL of MTT solution were added to designated wells in a prelabeled 24-well plate. The EpiOcular™ constructs were transferred to the appropriate wells after rinsing with $Ca_{++}Mg_{++}$Free-DPBS. The trays were incubated for approximately three hours at standard culture conditions. After the incubation period with MTT solution, the EpiOcular™ cultures were blotted on absorbent paper, cleared of excess liquid, and transferred to a prelabeled 24-well plate containing 2.0 mL of isopropanol in each designated well. The plates were sealed with parafilm and stored in the refrigerator (2-8° C.) until the last exposure time was harvested. The plates were then shaken for at least two hours at room temperature. At the end of the extraction period, the liquid within the cell culture inserts was decanted into the well from which the cell culture insert was taken. The extract solution was mixed and 200 μL were transferred to the appropriate wells of a 96-well plate. Two hundred microliters of isopropanol were added to the two wells designated as the blanks. The absorbance at 550 nm ($OD_{550}$) of each well was measured with a Molecular Devices Vmax plate reader.

The raw absorbance values were captured. The mean $OD_{550}$ of the blank wells was calculated. The corrected mean $OD_{550}$ values of the negative controls were determined by subtracting the mean $OD_{550}$ value of the blank wells from their mean $OD_{550}$ values. The corrected $OD_{550}$ values of the individual test article exposure times and the positive control exposure times were determined by subtracting the mean $OD_{550}$ value of the blank wells from their $OD_{550}$ values. All calculations were performed using an Excel spreadsheet. The following percent of control calculations were made:

$$\% \text{ of Control} = \frac{\text{corrected } OD_{550} \text{ of Test Article or Positive Control Exposure Time}}{\text{appropriate corrected mean } OD_{550} \text{ of Negative Control}} \times 100$$

Exposure time response curves were plotted with the % of Control on the ordinate and the test article or positive control exposure time on the abscissa. The $ET_{50}$ value was interpolated from each plot. To determine the $ET_{50}$, two consecutive points were selected, where one exposure time resulted in a relative survival greater than 50%, and one exposure time resulted in less than 50% survival. Two select points were used to determine the slope and the y-intercept for the equation y=m(x)+b. Finally, to determine the $ET_{50}$, the equation was solved for y=50. When all of the exposure time points showed greater than 50% survival, the $ET_{50}$ value was presented as greater than the longest test article exposure time ZAA Surfactants (E1-E7) Used in Inventive Compositions and Zwitterionic Surfactants Other than ZAA Surfactants (C1-C4) Used in Comparative Compositions:

Cocamidopropyl Betaine, Comparative Examples 1 and 4, were obtained from Evonik Inc. as Tego™ Betaine L7V and Tego™ Betaine F-50, respectively. Sodium Lauroamphoacetate, Comparative Example 2, was obtained from Solvay Inc. as Miranol™ HMD. Cocamidopropyl Hydroxysultaine, Comparative Example 3, was obtained from Solvay Inc. as Mirataine™ CBS.

Table 1 lists the ZAA surfactants according to Formula 1 used for Inventive Example Compositions and zwitterionic surfactants used in Comparative Compositions.

TABLE 1

| | INCI or Chemical Name | Trade Name | Activity (%) |
|---|---|---|---|
| E1 | 3-((4-(laurylamino)-4-oxobutyl)dimethylammonio)-2-hydroxypropane-1-sulfonate | N/A | 29.5* |
| E2 | 3-((4-(laurylamino)-4-oxobutyl)dimethylammonio)-propane-1-sulfonate | N/A | >99** |
| E3 | 3-((4-(lauryloxy)-4-oxobutyl)dimethylammonio)-2-hydroxypropane-1-sulfonate | N/A | 86** |
| E4 | 3-((4-(lauryloxy)-4-oxobutyl)dimethylammonio)-propane-1-sulfonate | N/A | >99** |
| E5 | 3-((2-(laurylamino)-2-oxoethyl)dimethylammonio)-propane-1-sulfonate | N/A | >99.5** |
| E6 | 3-((2-(lauryloxy)-2-oxoethyl)dimethylammonio)-propane-1-sulfonate | N/A | >99.5** |
| E7 | 3-((4-(coconylamino)-4-oxobutyl)dimethylammonio)-2-hydroxypropane-1-sulfonate | N/A | 31* |
| C1 | Cocamidopropyl Betaine | Tego ™ Betaine L7V | 30* |
| C2 | Sodium Lauroamphoacetate | Miranol ™ HMD | 27.5* |
| C3 | Cocamidopropyl Hydroxysultaine | Mirataine ™ CBS | 42* |
| C4 | Cocamidopropyl Betaine | Tego ™ Betaine F50 | 38* |

*Activity in water. The aqueous phase may also contain some amounts of sodium chloride and impurities, such as fatty acid, fatty alcohol or fatty amine.
**solid, may contain some amounts of sodium chloride and impurities, such as fatty alcohol or fatty amine.

The ZAA surfactants, E1-E7, noted in Table 1, were prepared as follows:

The Schematic Process Comprises:

(a) contacting an alcohol or amine or a mixture of alcohols or amines of Formula 4 with a dialkylamino-carboxylic acid or dialkylamino-carboxylic acid ester (amino acid derivative) of Formula 5:

Formula 4

Formula 5 in the presence of an enzyme at conditions effective to form an intermediate of Formula 6:

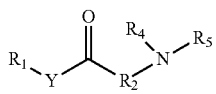

Formula 6 wherein Y, $R_1$, $R_2$, $R_4$, and $R_5$ are as defined above in Formula 1 and $R_7$ is hydrogen or $C_1$-$C_6$ alkyl; and (b) contacting the intermediate of Formula 6 with an alkylating agent at conditions effective to form the ZAA surfactant of Formula 1. Suitable alkylating agents are, for example, 2-chloro acetic acid or 2-hydroxy-3-chloro-propansulfonate or 1,3-propansultone.

As a specific example, the preparation of 3-((4-(laurylamino)-4-oxobutyl) dimethylammonio)-2-hydroxypropane-1-sulfonate is described:

Step a) Intermediate: lauryl 4-dimethylaminobutyramide

Ethyl 4-dimethylaminobutyrate (10 g; 62.8 mmol), laurylamine (11.64 g; 62.8 mmol; 1.0 equiv), and Novozym™ 435 (1.0 g) were combined and heated overnight at 65° C. with a nitrogen sparge. The mixture was filtered and the enzyme was washed with heptane. The filtrate was concentrated to afford lauryl 4-dimethylaminobutyramide (17.69 g; 94% yield).

Step b) Final Product: 3-((4-(laurylamino)-4-oxobutyl)dimethylammonio)-2-hydroxy propane-1-sulfonate, water solution Lauryl 4-dimethylaminobutyramide (12.5 g; 41.9 mmol), sodium 3-chloro-2-hydroxy propanesulfonate (95%, 9.15 g; 44.2 mmol; 1.06 equiv), and sodium carbonate (444 mg; 4.2 mmol; 0.1 equiv) were combined with 38.8 g of water and heated to 90° C. for 10 hours to afford 99.7% conversion to product according to HPLC analysis. The mixture was cooled to ambient temperature to afford 59.5 g of a very flowable solution.

The material was diluted with a little water and filtered through fine filter paper to afford a solution which analyzed at 24.9 wt % 3-((4-laurylamino-4-oxobutyl) dimethylammonio)-2-hydroxy-propanesulfonate.

The following compositions, Inventive Examples (E8-E68) and Comparative Examples (C5-C43) were prepared utilizing different types of formulation ingredients (i.e. raw materials from various suppliers) in addition to the ZAA surfactants. These materials, along with INCI names, trade names and suppliers are listed below:

Anionic Surfactants:
  Sodium Laureth-2 Sulfate was obtained from Solvay Inc. as Rhodapex™ ES-2K.
  Sodium Trideceth Sulfate was obtained from Solvay Inc. as Rhodapex™ EST-65.
  Ammonium Lauryl Sulfate was obtained from BASF as Standapol™ A.
  Alpha Olefin Sulfonate was obtained from Stepan as Bioterge™ AS 40-CP.
  Sodium Methyl-2 Sulfolaurate (SM2S) was obtained from Stepan as Alphastep™ PC-48.
  Sodium hydrolyzed Potato Starch Dodecenylsuccinate was obtained from Akzo Nobel Personal Care as Structure™ PS-111.

Non-Ionic Surfactants:
  Polysorbate 20 was obtained from Croda Inc Inc. as Tween™ 20.
  PEG-80 Sorbitan Laurate was obtained from Croda Inc. as Tween™ 28.
  PEG-150 Distearate was obtained from Ethox Chemical as Ethox™ PEG-6000 DS Special.
  The mixture of Coco-Glucoside, Glyceryl Oleate, water; citric acid, Hydrogenated
  Palm Glycerides Citrate, Tocopherol was obtained from BASF as Lamesoft™ PO 65.
  Coco-Glycoside and Decyl Glucoside were obtained from BASF as Plantacare™ 818 UP and Plantaren™ 2000 N, respectively.
  Polyglycerol-10 Laurate and Polyglycerol-10 Oleate were obtained from Lonza as
  Polyaldo™ 10-1-L and Polyaldo™ 10-1-O, respectively.

Pearlizer:
  Glycol Distearate; Sodium Laureth Sulfate; Myristyl Alcohol; water was obtained from Solvay Inc. as Mirasheen™ Star K.

Cationic (quaternary) conditioning polymers:
  Polyquaternium-10 was obtained from Dow Chemical as Ucare™ JR-400
  Guar Hydroxypropyltrimonium Chloride was obtained from Solvay Inc. as Jaguar™ C17.

Polymeric Rheology Modifiers:
  Acrylates/C10-30 Alkyl Acrylate Crosspolymer was obtained from Lubrizol as Carbopol™ ETD2020 or Carbopol™ 1382.

Humectants:
  Glycerin was obtained from Emery Oleochemicals as Emery™ 917.

Chelating Agents:
  Tetrasodium EDTA was obtained from Dow Chemical as Versene™ 100XL.

Organic Acids/Preservatives:
  Sodium Benzoate, NF, FCC was obtained from Emerald Performance Materials Citric acid was obtained from Formosa Laboratories Inc (for DSM) (Taiwan).
  Anisic acid was obtained from Dr. Straetmans Chemische Produkte GmbH as Dermsoft™ MM688.
  Tetrasodium Glutamate Diacetate was obtained from Akzo Nobel LLC as Dissolvine™ GL-475.

Preservatives:
  Phenoxyethanol and ethylhexylglycerin were obtained as a blend from Schülke Inc. as Euxyl™ PE 9010.
  Phenoxyethanol was obtained from Clariant as Phenoxetol™.
  Quaternium-15 was obtained from The Dow Chemical Company as Dowicil™ 200.

Benefit Agents:
  Avena Sativa Kernel Flour was obtained from Beacon CMP Corporation as Colloidal Oat Flour.
  Avena Sativa Kernel Extract was obtained from Ceapro Inc. as CP Oat Avenanthramide.
  Avena Sativa Kernel Oil was obtained from Symrise AG as Avena Lipid.
  Soybean Oil; Sunflower Oil was obtained from Textron Tecnica S. L. as EVOIL™ RM0604.

Inventive Examples E5-E18 and Comparative Examples C5-C14

Preparation and Measurement of Certain Compositions of the Invention with SLES as the Anionic Surfactant and Comparative Compositions Compositions E5-E18 and Comparative Compositions C5-C14 were made in accord with the following procedure:

Unless otherwise indicated, all materials were added in amounts such that the compositions contain resulting weight percent amounts of active as indicated for each composition in Tables 2, 3 and 4. For example, 3.75% w/w active of Cocamidopropyl Betaine (as given in table 2, C5) corresponds to 12.5% w/w Tego™ Betaine L7V, which has an activity of 30% w/w; 3.75% w/w/30% w/w=12.5% w/w.

Preparation of Stock Solutions: Compositions E5-E18 and Comparative Compositions C5-C14 were made using stock solutions, which had been prepared as follows: a) Stock with zwitterionic surfactant: To an appropriately sized vessel equipped with a hotplate and overhead mechanical stirrer, the required amount of DI water (Millipore, Model Direct Q), zwitterionic surfactant, and sodium chloride was added and mixed at 200-350 rpm until the mixture was homogeneous, for C1, E1 and E4 at room temperature, and for E2 at 50° C., respectively. Then, sodium benzoate and citric acid (20% w/w solution in DI water) were added at room temperature to adjust to the desired pH value 4.4-4.6. Water was added in q.s. to 100 wt %, and the batch was allowed to mix until uniform before being discharged to an appropriate storage vessel; b) Stock with anionic surfactant: To an appropriately sized vessel equipped with a hotplate and overhead mechanical stirrer, the required amount of DI water (Millipore, Model Direct Q), anionic surfactant, and citric acid were added and mixed at 200-350 rpm at room temperature until the mixture is homogeneous. An amount of citric acid (as 20% w/w solution in DI water) was added to adjust to the desired pH value 4.4-4.6. Water was added in q.s. to 100% w/w and the batch was allowed to mix until uniform before being discharged to an appropriate storage vessel.

Compositions E5-E18 and Comparative Compositions C5-C14 were made as follows: To an appropriately sized vessel equipped with a hotplate and overhead mechanical stirrer, the required amount of a) stock with zwitterionic surfactant and b) stock with anionic surfactant were added. Water was added in q.s. to 100% w/w. The batch was heated to 50° C. under mixing and mixed at 200-350 rpm for 20 minutes. The batch was allowed to cool to room temperature without mixing.

Tables 2-5 list Inventive Compositions (E8-E32) and Comparative Composition (C5-C17) made from the inventive ZAA surfactants (E1-E7) and comparative zwitterionic surfactants (C1, C2 and C4).

The Zero Shear Viscosity was measured in accord with the Zero Shear Viscosity Test as described herein. The results are shown in Table 6. As a result, applicants discovered that ZAA surfactants according to Formula 1 have the tendency to build higher viscosity in comparison to alkylamidoamine betaine surfactants in compositions containing Sodium Laureth Sulfate (SLES) as the anionic surfactant.

TABLE 2 a

| Material | Trade Name | Activity (%) | E8 wt. % | E9 wt. % | E10 wt. % | E11 wt. % | E12 wt. % | E13 wt. % | C5 wt. % | C6 wt. % |
|---|---|---|---|---|---|---|---|---|---|---|
| Weight ratio zwitterionic/amphoteric to anionic surfactant (active to active) | | | 0.71 | 0.71 | 0.71 | 0.71 | 0.71 | 0.71 | 0.71 | 0.71 |
| Zwitterionic (weight % active) | | | | | | | | | | |
| E1 | N/A | 29.5 | 3.75 | 3.75 | | | | | | |
| E2 | N/A | 99.5 | | | 3.75 | 3.75 | | | | |
| E3 | N/A | 86 | | | | | 3.75 | 3.75 | | |
| C4 | Tego™ Betaine F50 | 38 | | | | | | | 3.75 | 3.75 |
| Anionic (weight % active) | | | | | | | | | | |
| Sodium Laureth-2 Sulfate | Rhodapex™ ES-2K | 26 | 5.25 | 5.25 | 5.25 | 5.25 | 5.25 | 5.25 | 5.25 | 5.25 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0 | 1.25 | 0 | 1.25 | 0 | 1.25 | 0 | 1.25 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% | b

| Material | Trade Name | Activity (%) | E14 wt. % | E15 wt. % | E16 wt. % | E17 wt. % | E18 wt. % | E19 wt. % | E20 wt. % | E21 wt. % |
|---|---|---|---|---|---|---|---|---|---|---|
| Weight ratio zwitterionic/amphoteric to anionic surfactant (active to active) | | | 0.71 | 0.71 | 0.71 | 0.71 | 0.71 | 0.71 | 0.71 | 0.71 |
| Zwitterionic (weight % active) | | | | | | | | | | |
| E4 | N/A | 99.5 | 3.75 | 3.75 | | | | | | |
| E5 | N/A | 99.5 | | | 3.75 | 3.75 | | | | |
| E6 | N/A | 99.5 | | | | | 3.75 | 3.75 | | |
| E7 | N/A | 31 | | | | | | | 3.75 | 3.75 |

TABLE 2-continued

| | | | | | | | | | | |
|---|---|---|---|---|---|---|---|---|---|---|
| Anionic (weight % active) | | | | | | | | | | |
| Sodium Laureth-2 Sulfate | Rhodapex ™ ES-2K | 26 | 5.25 | 5.25 | 5.25 | 5.25 | 5.25 | 5.25 | 5.25 | 5.25 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0 | 1.25 | 0 | 1.25 | 0 | 1.25 | 0 | 1.25 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 3 a

| Material | Trade Name | Activity (%) | E22 wt. % | E23 wt. % | E24 wt. % | C7 wt. % | C8 wt. % | C9 wt. % |
|---|---|---|---|---|---|---|---|---|
| | Total Active | | 6 | 9 | 12 | 6 | 9 | 12 |
| Weight ratio zwitterionic/amphoteric to anionic surfactant (active to active) | | | 0.71 | 0.71 | 0.71 | 0.71 | 0.71 | 0.71 |
| Zwitterionic (weight % active) | | | | | | | | |
| E1 | N/A | 29.5 | 2.5 | 3.75 | 5 | | | |
| C4 | Tego ™ Betaine F50 | 38 | | | | 2.5 | 3.75 | 5 |
| Anionic (weight % active) | | | | | | | | |
| Sodium Laureth-2 Sulfate | Rhodapex ™ ES-2K | 26 | 3.5 | 5.25 | 7 | 3.5 | 5.25 | 7 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 0.75 | 0.75 | 0.75 | 0.75 | 0.75 | 0.75 |
| Water | Purified water, USP | 100 | Q.S. to 100% | Q.S. to 100% | Q.S. to 100% | Q.S. to 100% | Q.S. to 100% | Q.S. to 100% | b

| Material | Trade Name | Activity (%) | E25 wt. % | E26 wt. % | C10 wt. % | C11 wt. % |
|---|---|---|---|---|---|---|
| | Total Active | | 9 | 9 | 9 | 9 |
| Weight ratio zwitterionic/amphoteric to anionic surfactant (active to active) | | | 0.29 | 1.41 | 0.29 | 1.41 |
| Zwitterionic (weight % active) | | | | | | |
| E1 | N/A | 29.5 | 2 | 5.3 | | |
| C4 | Tego ™ Betaine F50 | 38 | | | 2 | 5.3 |
| Anionic (weight % active) | | | | | | |
| Sodium Laureth-2 Sulfate | Rhodapex ™ ES-2K | 26 | 7 | 3.75 | 7 | 3.75 |

TABLE 3-continued

| | | | Organic acids | | | |
|---|---|---|---|---|---|---|
| Sodium Benzoate | Sodium Benzoate, NF, FCC | 100 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 |
| | | | Other | | | |
| Sodium Chloride | Sodium Chloride, USP | 100 | 0 | 0 | 0 | 0 |
| Water | Purified water, USP | 100 | Q.S. to 100% | Q.S. to 100% | Q.S. to 100% | Q.S. to 100% |

TABLE 4

| Material | Trade Name | Activity (%) | E27 wt. % | E28 wt. % | C12 wt. % | C13 wt. % |
|---|---|---|---|---|---|---|
| Weight ratio zwitterionic/amphoteric to anionic surfactant (active to active) | | | 0.87 | 0.87 | 0.87 | 0.87 |
| | | Zwitterionic (weight % active) | | | | |
| E2 | N/A | 99.5 | 3.75 | | | |
| E4 | N/A | 99.5 | | 3.75 | | |
| C1 | Tego ™ Betaine L7V | 30 | | | 3.75 | |
| C2 | Miranol ™ HMD | 27.5 | | | | 3.75 |
| | | Anionic (weight % active) | | | | |
| Sodium Laureth-2 Sulfate | Rhodapex ™ ES-2K | 26 | 4.3 | 4.3 | 4.3 | 4.3 |
| | | Organic acids | | | | |
| Sodium Benzoate | Sodium Benzoate, NF, FCC | 100 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 |
| | | Other | | | | |
| Sodium Chloride | Sodium Chloride, USP | 100 | 0.75 | 0.75 | 0.75 | 0.75 |
| Water | Purified water, USP | 100 | Q.S. to 100% | Q.S. to 100% | Q.S. to 100% | Q.S. to 100% |

45

TABLE 5

| Material | Trade Name | Activity (%) | E29 wt. % | E30 wt. % | E31 wt. % | E32 wt. % | C14 wt. % | C15 wt. % | C16 wt. % | C17 wt. % |
|---|---|---|---|---|---|---|---|---|---|---|
| Weight ratio zwitterionic/amphoteric to anionic surfactant (active to active) | | | 0.71 | 0.71 | 0.71 | 0.71 | 0.71 | 0.71 | 0.71 | 0.71 |
| | | Zwitterionic (weight % active) | | | | | | | | |
| E3 | N/A | 86 | 3.75 | 3.75 | 3.75 | 3.75 | | | | |
| C4 | Tego ™ Betaine F50 | 38 | | | | | 3.75 | 3.75 | 3.75 | 3.75 |
| | | Anionic (weight % active) | | | | | | | | |
| Sodium Laureth-2 Sulfate | Rhodapex ™ ES-2K | 26 | 5.25 | 5.25 | 5.25 | 5.25 | 5.25 | 5.25 | 5.25 | 5.25 |
| | | Organic acids | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |

TABLE 5-continued

| Material | Trade Name | Activity (%) | E29 wt. % | E30 wt. % | E31 wt. % | E32 wt. % | C14 wt. % | C15 wt. % | C16 wt. % | C17 wt. % |
|---|---|---|---|---|---|---|---|---|---|---|
| Citric Acid | Citric Acid solution | 20 | Q.S. to pH 4.5 | Q.S. to pH 4.5 | Q.S. to pH 6 | Q.S. to pH 6 | Q.S. to pH 4.5 | Q.S. to pH 4.5 | Q.S. to pH 6 | Q.S. to pH 6 |
| Other |
| Sodium Chloride | Sodium Chloride, USP | 100 | 0 | 1.25 | 0 | 1.25 | 0 | 1.25 | 0 | 1.25 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 6

| Example | Viscosity (Cps) | Composition Information |
|---|---|---|
| E8 | 1581 | Ratio* 0.71, total active 9% w/w |
| E10 | 158 | 3.75% w/w zwitterionic surfactant |
| E12 | 41750 | 5.25% w/w anionic surfactant (SLES) |
| E14 | 18660 | 0% w/w sodium chloride |
| E16 | 1039 | |
| E18 | 158 | |
| E20 | 940 | |
| C5 | 10 | |
| E9 | 114400 | Ratio 0.71, total active 9% w/w |
| E11 | 282600 | 3.75% w/w zwitterionic surfactant |
| E13 | 264800 | 5.25% w/w anionic surfactant (SLES) |
| E15 | 180200 | 1.25% w/w sodium chloride |
| E17 | n/a | |
| E19 | 1172 | |
| E21 | 300000 | |
| C6 | 9478 | |
| E22 | 16060 | Ratio 0.71, total active 6% w/w |
| C7 | 74 | 2.5% w/w zwitterionic surfactant |
| | | 3.5% w/w anionic surfactant (SLES) |
| | | 0.75% w/w sodium chloride |
| E23 | 126100 | Ratio 0.71, total active 9% w/w |
| C8 | 1023 | 3.75% w/w zwitterionic surfactant |
| | | 5.25% w/w anionic surfactant (SLES) |
| | | 0.75% w/w sodium chloride |
| E24 | 283800 | Ratio 0.71, total active 12% w/w |
| C9 | 6356 | 5% w/w zwitterionic surfactant |
| | | 7% w/w anionic surfactant (SLES) |
| | | 0.75% w/w sodium chloride |
| E25 | 10 | Ratio 0.29, total active 9% w/w |
| C10 | 10 | 2% w/w zwitterionic surfactant |
| | | 7% w/w anionic surfactant (SLES) |
| | | 0% w/w sodium chloride |
| E26 | 397700 | Ratio 1.41, total active 9% w/w |
| C11 | 700 | 5.3% w/w zwitterionic surfactant |
| | | 3.75% w/w anionic surfactant (SLES) |
| | | 0% w/w sodium chloride |
| E27 | 41850 | Ratio 0.87, total active 8% w/w |
| E28 | 118000 | 3.75% w/w/ zwitterionic surfactant |
| C12 | 6708 | 4.3% w/w/ anionic surfactant (SLES) |

TABLE 6-continued

| Example | Viscosity (Cps) | Composition Information |
|---|---|---|
| C13 | 355 | 0.75% w/w sodium chloride |
| E29 | 41750 | pH 6, ratio 0.71, total active 9% w/w |
| E31 | 7011 | 3.75% w/w zwitterionic surfactant |
| C14 | 10 | 5.25% w/w anionic surfactant (SLES) |
| C15 | 10 | 0% w/w sodium chloride |
| E30 | 264800 | pH 6, ratio 0.71, total active 9% w/w |
| E32 | 350400 | 3.75% w/w zwitterionic surfactant |
| C16 | 9478 | 5.25% w/w anionic surfactant (SLES) |
| C17 | 2106 | 1.25% w/w sodium chloride |

*Ratio: weight ratio zwitterionic/amphoteric surfactant to anionic surfactant (active to active)

Inventive Examples E33-E38 and Comparative Examples C18-C19

Preparation and Measurement of Certain Compositions of the Invention with ALS as the Anionic Surfactant and Comparative Compositions Inventive Compositions E33-E38 and Comparative Compositions C18-19 were made in accord with the procedure described for Compositions E7-E32 and Comparative Compositions C5-C17, except that ALS (Standapol™ A) was used as the anionic surfactant instead of SLES (Rhodapex™ ES-2K). Table 7 lists such compositions.

The Zero Shear Viscosity were measured in accord with the Zero Shear Viscosity Test as described herein. The results are shown in Table 8. As a result, applicants discovered that ZAA surfactants have the tendency to build equivalent or higher viscosity in comparison to alkylamidoamine betaine surfactants in compositions containing Ammonium Lauryl Sulfate as the anionic surfactant, especially at salt concentrations from 0% w/w to around 1% w/w added sodium chloride.

TABLE 7

| Material | Trade Name | Activity (%) | E33 wt. % | E34 wt. % | E35 wt. % | E36 wt. % | E37 wt. % | E38 wt. % | C18 wt. % | C19 wt. % |
|---|---|---|---|---|---|---|---|---|---|---|
| Total active surfactant (weight %) | | | 9 | 9 | 9 | 9 | 9 | 9 | 9 | 9 |
| Weight ratio zwitterionic/amphoteric to anionic surfactant (active to active) | | | 0.71 | 0.29 | 0.71 | 0.29 | 0.71 | 0.29 | 0.71 | 0.29 |
| Zwitterionic (weight % active) |
| E1 | N/A | 29.5 | 3.75 | 2 | | | | | | |
| E2 | N/A | 99.5 | | | 3.75 | 2 | | | | |
| E3 | N/A | 86 | | | | | 3.75 | 2 | | |
| C4 | Tego ™ Betaine F50 | 38 | | | | | | | 3.75 | 2 |

TABLE 7-continued

| Material | Trade Name | Activity (%) | E33 wt. % | E34 wt. % | E35 wt. % | E36 wt. % | E37 wt. % | E38 wt. % | C18 wt. % | C19 wt. % |
|---|---|---|---|---|---|---|---|---|---|---|
| Anionic (weight % active) | | | | | | | | | | |
| Ammonium Lauryl Sulfate | Standapol™ A | 28 | 5.25 | 7 | 5.25 | 7 | 5.25 | 7 | 5.25 | 7 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0 | 0.75 | 0 | 0.75 | 0 | 0.75 | 0 | 0.75 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 8

| Example | Viscosity (Cps) | Composition Information |
|---|---|---|
| E33 | 90290 | Ratio zw/an 0.71, total active 9% w/w |
| E35 | 101400 | 3.75% w/w zwitterionic surfactant |
| E37 | 4236 | 5.25% w/w anionic surfactant (ALS) |
| C18 | 1 | 0% w/w sodium chloride |
| E34 | 3896 | Ratio zw/an 0.29, total active 9% w/w |
| E36 | 7904 | 2% w/w zwitterionic surfactant |
| E38 | 7890 | 7% w/w anionic surfactant (ALS) |
| C19 | 38 | 0.75% w/w sodium chloride |

Inventive Examples E39-44 and Comparative Examples C20-25

Preparation and Measurement of Certain Compositions of the Invention with AOS as the Anionic Surfactant and Comparative Compositions Compositions E39-44 and Comparative Compositions C20-25 were made in accord with the procedure described for Compositions E8-E32 and Comparative Compositions C5-C17, except that AOS (Bioterge™-AS 40-CP) was used as the anionic surfactant instead of SLES (Rhodapex™ ES-2K). Table 9 and 10 list such compositions.

The Zero Shear Viscosity was measured in accord with the Zero Shear Viscosity Test as described herein. The results are shown in Table 11. As a result and surprisingly, applicants discovered that ZAA surfactants can build viscosity in compositions containing AOS as the anionic surfactant, whereas alkylamido betaine surfactants cannot.

TABLE 9

| Material | Trade Name | Activity (%) | E39 wt. % | E40 wt. % | E41 wt. % | C20 wt. % | C21 wt. % | C22 wt. % |
|---|---|---|---|---|---|---|---|---|
| Weight ratio zwitterionic/amphoteric to anionic surfactant (active to active) | | | 0.29 | 0.71 | 1.41 | 0.29 | 0.71 | 1.41 |
| Zwitterionic (weight % active) | | | | | | | | |
| E1 | N/A | 29.5 | 2 | 3.75 | 5.3 | | | |
| C4 | Tego™ Betaine F50 | 38 | | | | 2 | 3.75 | 5.3 |
| Anionic (weight % active) | | | | | | | | |
| Alpha Olefin Sulfonate | Bioterge™-AS 40-CP | 39 | 7 | 5.25 | 3.75 | 7 | 5.25 | 3.75 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 0.75 | 0.75 | 0.75 | 0.75 | 0.75 | 0.75 |
| Water | Purified water, USP | 100 | Q.S. to 100% | Q.S. to 100% | Q.S. to 100% | Q.S. to 100% | Q.S. to 100% | Q.S. to 100% |

TABLE 10

| Material | Trade Name | Activity (%) | E42 wt. % | E43 wt. % | E44 wt. % | C23 wt. % | C24 wt. % | C25 wt. % |
|---|---|---|---|---|---|---|---|---|
| Weight ratio zwitterionic/amphoteric to anionic surfactant (active to active) | | | 0.71 | 0.71 | 0.71 | 0.71 | 0.71 | 0.71 |
| Zwitterionic (weight % active) | | | | | | | | |
| E3 | N/A | 86 | 3.75 | 3.75 | 3.75 | | | |
| C4 | Tego ™ Betaine F50 | 38 | | | | 3.75 | 3.75 | 3.75 |
| Anionic (weight % active) | | | | | | | | |
| Alpha Olefin Sulfonate | Bioterge ™- AS 40-CP | 39 | 5.25 | 5.25 | 5.25 | 5.25 | 5.25 | 5.25 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 0 | 0.75 | 1.25 | 0 | 0.75 | 1.25 |
| Water | Purified water, USP | 100 | Q.S. to 100% | Q.S. to 100% | Q.S. to 100% | Q.S. to 100% | Q.S. to 100% | Q.S. to 100% |

TABLE 11

| Example | Viscosity (Cps) | Composition Information |
|---|---|---|
| E39 | 10 | 2% w/w zwitterionic surfactant |
| C20 | 10 | 7% w/w anionic surfactant (AOS) 0.75% w/w sodium chloride |
| E40 | 32350 | 3.75% w/w zwitterionic surfactant |
| C21 | 10 | 5.25% w/w anionic surfactant (AOS) 0.75% w/w sodium chloride |
| E41 | 257900 | 5.3% w/w zwitterionic surfactant |
| C22 | 446 | 3.75% w/w anionic surfactant (AOS) 0.75% w/w sodium chloride |
| E42 | 1422 | 3.75% w/w zwitterionic surfactant |
| C23 | 10 | 5.25% w/w anionic surfactant (AOS) 0% w/w sodium chloride |
| E43 | 148600 | 3.75% w/w zwitterionic surfactant |
| C24 | 10 | 5.25% w/w anionic surfactant (AOS) 0.75% w/w sodium chloride |
| E44 | 390400 | 3.75% w/w zwitterionic surfactant |
| C25 | 10 | 5.25% w/w anionic surfactant (AOS) 1.25% w/w sodium chloride |

Inventive Examples E45-E52 and Comparative Examples C26-C33

Preparation and Measurement of Certain Compositions of the Invention with and without PS-111 as an Anionic Surfactant and Comparative Compositions Compositions E45-E52 and Comparative Compositions C26-C33 were made in accord with the following procedure:

Unless otherwise indicated, all materials were added in amounts such that the compositions contain resulting weight percent amounts of active as indicated for each composition in Tables 12 and 14. For example, 3.75% w/w active of Cocamidopropyl Betaine (as given in table 12, C26) corresponds to 12.5% w/w Tego™ Betaine L7V, which has an activity of 30% w/w; 3.75% w/w/30% w/w=12.5% w/w.

Compositions E45-E52 and Comparative Compositions C26-C33 were made as follows: To an appropriately sized vessel equipped with a hotplate and overhead mechanical stirrer, the required amount of DI water, zwitterionic surfactant, anionic surfactant, and sodium benzoate are added and mixed at room temperature with 200-350 rpm until the mixture is homogeneous. Then, citric acid (20% w/w solution in DI water) is added at room temperature to adjust to the desired pH value 4.4-4.6. Then, Structure PS-111 and Sodium chloride are added and mixed until the mixture is homogeneous. Water was added in q.s. to 100 wt %, and the batch is allowed to mix until uniform before being discharged to an appropriate storage vessel. Tables 12 and 14 list such compositions.

The Zero Shear Viscosity and Maximum Foam Volume were measured in accord with the Zero Shear Viscosity Test and Formulation Foam Test, respectively, as described herein. The results are shown in Table 13 and 15. As a result and surprisingly, applicants discovered that ZAA surfactants can not only build viscosity in compositions containing AOS and/or SM2S as the anionic surfactant, but that such compositions also exhibit better foamability compared to compositions with zwitterionic alkylamidoamine betaine surfactants.

TABLE 12

| Material | Trade Name | Activity (%) | E45 wt. % | E46 wt. % | E47 wt. % | E48 wt. % | C26 wt. % | C27 wt. % | C28 wt. % | C29 wt. % |
|---|---|---|---|---|---|---|---|---|---|---|
| Zwitterionic (weight % active) | | | | | | | | | | |
| E7 | N/A | 31 | 3.75 | 3.75 | 3.75 | 3.75 | | | | |
| C1 | Tego ™ Betaine L7V | 30 | | | | | 3.75 | 3.75 | 3.75 | 3.75 |

TABLE 12-continued

| Material | Trade Name | Activity (%) | E45 wt. % | E46 wt. % | E47 wt. % | E48 wt. % | C26 wt. % | C27 wt. % | C28 wt. % | C29 wt. % |
|---|---|---|---|---|---|---|---|---|---|---|
| Anionic (weight % active) | | | | | | | | | | |
| AOS | Bioterge ™ AS-40 | 39 | 3.75 | 3.75 | | | 3.75 | 3.75 | | |
| SM2S | Alphastep ™ PC-48 | 37 | | | 2.25 | 2.25 | | | 2.25 | 2.25 |
| Sodium Hydrolyzed Potato Starch Dodecenyl-Succinate | Structure ™ PS-111 | 94 | | 3 | | 3 | | 3 | | 3 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0.6 | 0.6 | 0.2 | 0.2 | 0.6 | 0.6 | 0.2 | 0.2 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 13

| Example | Viscosity (cps) | Foam Volume (ml) | Composition Information |
|---|---|---|---|
| E45 | 406700 | 352 | 3.75% w/w zwitterionic surfactant |
| C26 | 34 | 269 | 3.75% w/w anionic surfactant (AOS) 0% w/w Structure ™ PS-111 0.6% w/w sodium chloride |
| E46 | 37890 | 356 | 3.75% w/w zwitterionic surfactant |
| C27 | 75 | 280 | 3.75% w/w anionic surfactant (AOS) 3% w/w Structure ™ PS-111 0.6% w/w sodium chloride |
| E47 | 19030 | 332 | 3.75% w/w zwitterionic surfactant |
| C28 | 4 | 154 | 2.25% w/w anionic surfactant (SM2S) 0% w/w Structure ™ PS-111 0.2% w/w sodium chloride |
| E48 | 2045 | 380 | 3.75% w/w zwitterionic surfactant |
| C29 | 30 | 280 | 2.25% w/w anionic surfactant (SM2S) 3% w/w Structure ™ PS-111 0.2% w/w sodium chloride |

TABLE 14

| Material | Trade Name | Activity (%) | E49 wt. % | E50 wt. % | E51 wt. % | E52 wt. % | C30 wt. % | C31 wt. % | C32 wt. % | C33 wt. % |
|---|---|---|---|---|---|---|---|---|---|---|
| Zwitterionic (weight % active) | | | | | | | | | | |
| E7 | N/A | 29.7 | 3.75 | 3.75 | 3.75 | 3.75 | | | | |
| C1 | Tego ™ Betaine L7V | 30 | | | | | 3.75 | 3.75 | 3.75 | 3.75 |
| Anionic (weight % active) | | | | | | | | | | |
| AOS | Bioterge ™ AS 40-CP | 39 | 5.75 | 5.75 | | | 5.75 | 5.75 | | |
| SM2S | Alphastep ™ PC-48 | 37 | | | 3.74 | 3.74 | | | 3.74 | 3.74 |
| Sodium Hydrolyzed Potato Starch Dodecenyl-Succinate | Structure ™ PS-111 | 94 | | 3 | | 3 | | 3 | | 3 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 1.45 | 1.45 | 0.2 | 0.2 | 1.45 | 1.45 | 0.2 | 0.2 |

TABLE 14-continued

| Material | Trade Name | Activity (%) | E49 wt. % | E50 wt. % | E51 wt. % | E52 wt. % | C30 wt. % | C31 wt. % | C32 wt. % | C33 wt. % |
|---|---|---|---|---|---|---|---|---|---|---|
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 15

| Example | Viscosity (Cps) | Foam Volume (ml) | Composition Information |
|---|---|---|---|
| E49 | 106200 | 436 | 3.75% w/w zwitterionic surfactant |
| C30 | 175 | 307 | 5.75% w/w anionic surfactant (AOS) 0% w/w Structure™ PS-111 1.45% w/w sodium chloride |
| E50 | 72330 | 458 | 3.75% w/w zwitterionic surfactant |
| C31 | 348 | 353 | 5.75% w/w anionic surfactant (AOS) 3% w/w Structure™ PS-111 1.45% w/w sodium chloride |
| E51 | 286 | 418 | 3.75% w/w zwitterionic surfactant |
| C32 | 1 | 154 | 3.74% w/w anionic surfactant (SM2S) 0% w/w Structure™ PS-111 0.2% w/w sodium chloride |
| E52 | 95 | 411 | 3.75% w/w zwitterionic surfactant |
| C33 | 4 | 257 | 3.74% w/w anionic surfactant (SM2S) 3% w/w Structure™ PS-111 0.2% w/w sodium chloride |

Inventive Example E53 and Comparative Example C34

Preparation and Measurement of Certain Compositions of the Invention with Conditioning Polymer and Comparative Compositions Composition E53 and Comparative Composition C34 were made in accord with the following procedure: Unless otherwise indicated, all materials were added in amounts such that the compositions contain resulting weight percent amounts of active as indicated for each composition in Table 16. For example, 5% w/w active of Cocamidopropyl Betaine (as given in table 16, C34) corresponds to 13.2% w/w Tego™ Betaine F50, which has an activity of 38% w/w; 5% w/w/38% w/w=13.2% w/w.

Composition E53 and Comparative Composition C34 were made as follows: To an appropriately sized vessel equipped with a hotplate and overhead mechanical stirrer, 90% of the required amount of DI water was added, stirred at 200-350 rpm. Oat flour was added and mixed until completely dispersed. Ucare™ JR-400 was added and mixed for 10 mins. Batch was heated to 50° C. Zwitterionic/amphoteric surfactant and Rhodapex™ ES-2K were added one by one and mixed until uniform. Glycerin and tetrasodium EDTA were added to the main batch. Dowicil™ 200 was added and mixed until uniform. Mirasheen™ Star K and Avena sativa kernel extract, Avena Lipid and Evoil™ were added one by one and mixed until uniform. Fragrance was added and the pH adjusted to 6.3-7.3 (target 6.4-6.7). Water was added in q.s. to 100 wt %, and the batch is allowed to mix until uniform before being discharged to an appropriate storage vessel. Table 16 lists such compositions.

The Zero Shear Viscosity and Maximum Foam Volume were measured in accord with the Zero Shear Viscosity Test and Formulation Foam Test, respectively, as described herein. The results are shown in Table 17. As a result and surprisingly, applicants discovered that ZAA surfactants have the tendency to build equivalent or higher viscosity in comparison to zwitterionic alkylamidoamine betaine surfactants in compositions containing cationic conditioning polymers and that such compositions also exhibit better foamability compared to compositions with zwitterionic alkylamidoamine betaine surfactants.

TABLE 16

| Material | Trade Name | Activity (%) | E53 wt. % | C34 wt. % |
|---|---|---|---|---|
| E7 | N/A | 31 | 5 | |
| C4 | Tego™ Betaine F50 | 38 | | 5 |
| Sodium Laureth Sulfate | Rhodapex™ ES-2k | 26 | 3.9 | 3.9 |
| Glycol Distearate; Sodium Laureth Sulfate; Myristyl Alcohol; water | Mirasheen™ Star K | 100 | 1.5 | 1.5 |
| Guar Hydroxypropyltrimonium Chloride | Jaguar™ C17 | 100 | 0.5 | 0.5 |
| Polyquaternium-10 | Ucare™ JR-400 | 100 | 0.2 | 0.2 |
| Glycerin | Glycerin 917 Kosher | 100 | 6 | 6 |
| Avena Sativa Kernel Flour | Colloidal Oat Flour | 100 | 1 | 1 |
| Avena Sativa Kernel Extract; Glycerin; Water | CP Oat Avenanthramide | 100 | 0.01 | 0.01 |
| Avena Sativa Kernel Oil | Avena Lipid | 100 | 0.01 | 0.01 |
| Soybean Oil; Sunflower Oil | EVOIL™ RM0604 | 100 | 0.01 | 0.01 |
| Fragrance | Fragrance | 100 | 0.45 | 0.45 |
| Tetrasodium EDTA | Versene™ 100 XL | 100 | 0.8 | 0.8 |
| Quaternium-15 | Dowicil™ 200 | 100 | 0.05 | 0.05 |
| Sodium Hydroxide | NaOH solution | 32 | Q.S. to pH 4.5 | Q.S. to pH 4.5 |
| Citric Acid | Citric Acid solution | 20 | Q.S. to pH 4.5 | Q.S. to pH 4.5 |
| Water | Purified water, USP | 100 | Q.S. to 100% | Q.S. to 100% |

TABLE 17

| Example | Viscosity (cps) | Foam Volume (ml)* |
|---|---|---|
| E53 | 19600 | 277 |
| C34 | 20300 | 194 |

*Tested at 0.1 wt % in simulated hard water.

Inventive Examples E54-E57 and Comparative Examples C35-C36

Preparation and Measurement of Certain Compositions of the Invention with PS-111 and Nonionic Surfactants and Comparative Compositions Compositions E54-E57 and Comparative Compositions C35-C36 were made in accord with the following procedure: Unless otherwise indicated, all materials were added in amounts such that the compositions contain resulting weight percent amounts of active as indicated for each composition in Table 18. For example, 3.75% w/w active of Cocamidopropyl Betaine (as given in table 18, C35) corresponds to 12.5% w/w Tego™ Betaine L7V, which has an activity of 30% w/w; 3.75% w/w/30% w/w=12.5% w/w. Compositions E54-E57 and Comparative Compositions C35-C36 were made as follows: To an appropriately sized vessel equipped with a hotplate and overhead mechanical stirrer, 90% of the required amount of DI water, zwitterionic, anionic surfactants (Rhodapex™ ES-2K and, Structure™ PS-111), and the Polyaldo™ surfactant were added and the batch was mixed at 200-350 rpm until the mixture was homogeneous. Citric acid (20% w/w solution in DI water) was added to adjust to the desired pH value 4.4-4.6. Sodium benzoate and sodium chloride were added. Water was added in q.s. to 100 wt %, and the batch is allowed to mix until uniform before being discharged to an appropriate storage vessel. Table 18 lists such compositions.

The Zero Shear Viscosity and Maximum Foam Volume were measured in accord with the Zero Shear Viscosity Test and Formulation Foam Test, respectively, as described herein. The results are shown in Table 19. As a result, applicants discovered that ZAA surfactants have the tendency to build higher viscosity in comparison to zwitterionic alkylamidoamine betaine surfactants in compositions containing anionic surfactants and several other formulation ingredients, like polyglycerol ester surfactants. Such compositions also exhibit equivalent or better foamability in comparison to the equivalent compositions containing zwitterionic alkylamidoamine betaine surfactants.

TABLE 18

| Material | Trade Name | Activity (%) | E54 wt. % | E55 wt. % | E56 wt. % | E57 wt. % | C35 wt. % | C36 wt. % |
|---|---|---|---|---|---|---|---|---|
| Weight ratio zwitterionic/amphoteric to anionic surfactant (active to active) | | | 0.51 | 0.51 | 0.51 | 0.51 | 0.51 | 0.51 |
| Zwitterionic (weight % active) | | | | | | | | |
| E1 | N/A | | 3.75 | 3.75 | | | | |
| E4 | N/A | 29.7 | | | 3.75 | 3.75 | | |
| C1 | Tego™ Betaine L7V | 30 | | | | | 3.75 | 3.75 |
| Anionic (weight % active) | | | | | | | | |
| Sodium Laureth-2 Sulfate | Rhodapex™ ES-2K | 26 | 6.3 | 6.3 | 6.3 | 6.3 | 6.3 | 6.3 |
| PS-111 | Structure™ PS-111 | | 1 | 1 | 1 | 1 | 1 | 1 |
| Nonionic (weight % active) | | | | | | | | |
| | Polyaldo™ 10-1-L | 100 | 1 | | 1 | | 1 | |
| | Polyaldo™ 10-1-O | 100 | | 1 | | 1 | | 1 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 1.22 | 1.22 | 1.22 | 1.22 | 1.22 | 1.22 |
| Water | Purified water, USP | 100 | Q.S. to 100% | Q.S. to 100% | Q.S. to 100% | Q.S. to 100% | Q.S. to 100% | Q.S. to 100% |

TABLE 19

| Example | Viscosity (Cps) | Foam Volume (ml) |
|---|---|---|
| E54 | 82210 | 406 |
| E56 | 43240 | 479 |
| C35 | 25240 | 390 |
| E55 | 55630 | 446 |
| E57 | 123000 | 488 |
| C36 | 16490 | 359 |

Example E58-E61 and Comparative Example C37

Preparation and Measurement of Certain Compositions of the Invention Containing No Anionic Surfactant and Comparative Compositions Compositions E58-E61 and Comparative Composition C37 were made in accord with the following procedure: All materials were added in amounts as indicated for each composition in Tables 20. For example, 2.4% w/w active of 3-((4-(laurylamino)-4-oxobutyl)dimethylammonio)-2-hydroxypropane-1-sulfonate (as given in table 20, E58) corresponds to 8.1% w/w E1, which has an activity of 29.5% w/w; 2.4% w/w/29.5% w/w=8.1% w/w.

malized to the same surfactant concentrations (% w/w active) as corresponding Inventive Examples (C37 correspond to E58-E61).

TABLE 20

| Material | Trade Name | Activity (%) | E58 wt. % | E59 wt. % | E60 wt. % | E61 wt. % | C37 wt. % |
|---|---|---|---|---|---|---|---|
| E1 | N/A | 29.5 | 2.4 | | | | |
| E2 | N/A | 99.5 | | 2.4 | | | |
| E3 | N/A | 86 | | | 2.4 | | |
| E4 | N/A | 99.5 | | | | 2.4 | |
| C4 | Tego ™ Betaine F50 | 38 | | | | | 2.4 |
| Coco-Glucoside; Glyceryl Oleate; Water; Citric Acid;; Hydrogenated Palm Glycerides Citrate; Tocopherol | Lamesoft ™ PO65 | 100 | 1 | 1 | 1 | 1 | 1 |
| Coco-Glycoside | Plantacare ™ 818 UP | 52 | 8.3 | 8.3 | 8.3 | 8.3 | 8.3 |
| Acrylates/C10-30 Alkyl Acrylate Crosspolymer | Carbopol ™ ETD 2020 | 100 | 0.6 | 0.6 | 0.6 | 0.6 | 0.6 |
| Anisic Acid | Dermosoft ™ MM688 | 100 | 0.2 | 0.2 | 0.2 | 0.2 | 0.2 |
| Fragrance | Fragrance | 100 | 0.1 | 0.1 | 0.1 | 0.1 | 0.1 |
| Sodium Benzoate | Sodium Benzoate, NF, FCC | 100 | 0.5 | 0.5 | 0.5 | 0.5 | 0.5 |
| Phenoxy Ethanol | Phenoxetol ™ | 100 | 0.7 | 0.7 | 0.7 | 0.7 | 0.7 |
| Sodium Hydroxide | NaOH solution | 32 | Q.S. to pH 5.5 | Q.S. to pH 5.5 | Q.S. to pH 5.5 | Q.S. to pH 5.5 | Q.S. to pH 5.5 |
| Citric Acid | Citric Acid solution | 20 | Q.S. to pH 5.5 | Q.S. to pH 5.5 | Q.S. to pH 5.5 | Q.S. to pH 5.5 | Q.S. to pH 5.5 |
| Water | Purified water, USP | 100 | Q.S. to 100% | Q.S. to 100% | Q.S. to 100% | Q.S. to 100% | Q.S. to 100% |

Compositions E58-E61 and Comparative Composition C37 were made as follows: To an appropriately sized vessel equipped with a hotplate and overhead mechanical stirrer, 50% of the required amount of DI water was added, stirred at 200-350 rpm. Add 0.05% w/w citric acid to adjust pH to 3-3.5. The Carbopol™ ETD2020 was sifted slowly into the vortex. The mixture was heated to 60° C. and stirred until the polymer was fully dispersed. The zwitterionic surfactant (e.g. E1 or Tego™ Betaine F50) and then sodium benzoate were added to the mixture and stirred until uniform. Dermosoft™ 688 was added and the mixture homogenized for 10 min. The pH was adjusted to 5.1-5.5 by adding 50% w/w NaOH in water. Cooling to 30° C. was started and 20% of the DI water was added for faster cooling. Phenoxyethanol, Plantacare™ 818UP, Lamesoft™ PO65 and fragrance were added with homogenization after each step. The pH was adjusted to 5.5-5.8. Water was added in q.s. to 100 wt %, and the batch is allowed to mix until uniform before being discharged to an appropriate storage vessel. Compositions prepared are listed in Table 20.

The Zero Shear Viscosity and Maximum Foam Volume were measured in accord with the Zero Shear Viscosity Test and Formulation Foam Test, respectively, as described herein. The results are shown in Table 21. As a result, applicants discovered that ZAA surfactants have the tendency to build higher viscosity in comparison to zwitterionic alkylamidoamine betaine surfactants in compositions containing no anionic surfactants, but several other formulation ingredients. Such compositions also exhibit equivalent or better foamability in comparison to the equivalent compositions containing zwitterionic alkylamidoamine betaine surfactants. Applicants note the comparative example is nor-

TABLE 21

| Example | Viscosity (cps) | Foam Volume (ml)* |
|---|---|---|
| E58 | 19520 | 225 |
| E59 | 35570 | 252 |
| E60 | 21130 | 235 |
| E61 | 39750 | 262 |
| C37 | 12800 | 185 |

*Tested at 0.1 wt % in simulated hard water.

Inventive Examples E62-E67 and Comparative Example C38-C41

Preparation and Measurement of Certain Compositions of the Invention Equivalent to Commercial Formulations Compositions E62-E65 and Comparative Composition C38 were made in accord with the following procedure: All materials were added in amounts as indicated for each composition in Tables 22. For example, 2.7% w/w active of 3-((4-(laurylamino)-4-oxobutyl)dimethylammonio)-2-hydroxypropane-1-sulfonate (as given in table 22, E62) corresponds to 9.2% w/w E1, which has an activity of 29.5% w/w; 2.7% w/w/29.5% w/w=9.2% w/w.

Compositions E62-E65 and Comparative Composition C38 were made as follows: To an appropriately sized vessel equipped with a hotplate and overhead mechanical stirrer, 90% of the required amount of DI water was added, stirred at 200-350 rpm. The Carbopol™ 1382 was sifted slowly into the vortex. The mixture was stirred until the polymer was fully dispersed. Sodium benzoate was added to the mixture and stirred until uniform. After adding glycerin, the batch was heated to 65-70° C. The pH was adjusted to 6.0-6.5 by adding 50% w/w NaOH in water. Plantaren™ 2000 N; zwitterionic surfactant (e.g. E1 or Tego™ Betain F50); Lamesoft™ PO 65; Polyaldo™ 10-1-L had been added one by one under stirring mixed until uniform. The heating was removed and the mixture was allowed to cool. At 55-60° C. Euxyl™ PE9010 was added. The pH was adjusted to 5.3-5.8. Water was added in q.s. to 100 wt %, and the batch is allowed to mix until uniform before being discharged to an appropriate storage vessel. Compositions prepared are listed in Table 22.

The Zero Shear Viscosity and Maximum Foam Volume were measured in accord with the Zero Shear Viscosity Test and Formulation Foam Test, respectively, as described herein. The results are shown in Table 23. As a result, applicants discovered that ZAA surfactants have the tendency to build higher viscosity in comparison to alkylamidoamine betaine surfactants in compositions containing no anionic surfactants. Such compositions also exhibit equivalent or better foamability in comparison to the equivalent compositions containing zwitterionic alkylamidoamine betaine surfactants. Applicants note the comparative examples are normalized to the same surfactant concentrations (% w/w active) as corresponding Inventive Examples (C38 corresponds to E62-E65).

TABLE 22

| Material | Trade Name | Activity (%) | E62 wt. % | E63 wt. % | E64 wt. % | E65 wt. % | C38 wt. % |
|---|---|---|---|---|---|---|---|
| E1 | N/A | 29.5 | 2.7 | | | | |
| E2 | N/A | 99.5 | | 2.7 | | | |
| E3 | N/A | 86 | | | 2.7 | | |
| E4 | N/A | 99.5 | | | | 2.7 | |
| C4 | Tego ™ Betaine F50 | 38 | | | | | 2.7 |
| Coco-Glucoside; Glyceryl Oleate; Water; Citric Acid; Hydrogenated Palm Glycerides Citrate; Tocopherol | Lamesoft ™ PO65 | 100 | 1 | 1 | 1 | 1 | 1 |
| Polyglycerol-10 Laurate | Polyaldo ™ 10-1-L | 100 | 1 | 1 | 1 | 1 | 1 |
| Decyl Glucoside | Plantaren ™ 2000 N | 49 | 6.9 | 6.9 | 6.9 | 6.9 | 6.9 |
| Acrylates/C10-30 Alkyl Acrylate Crosspolymer | Carbopol ™ 1382 | 100 | 0.6 | 0.6 | 0.6 | 0.6 | 0.6 |
| Glycerin | Glycerin 99.7 Kosher | 100 | 1 | 1 | 1 | 1 | 1 |
| Fragrance | Fragrance | 100 | 0.04 | 0.04 | 0.04 | 0.04 | 0.04 |
| Sodium Benzoate | Sodium Benzoate, NF, FCC | 100 | 0.5 | 0.5 | 0.5 | 0.5 | 0.5 |
| Phenoxy Ethanol and Ethylhexyl-glycerin | Euxyl ™ PE 9010 | 100 | 0.9 | 0.9 | 0.9 | 0.9 | 0.9 |
| Sodium Hydroxide | NaOH solution | 32 | Q.S. to pH 5.5 | Q.S. to pH 5.5 | Q.S. to pH 5.5 | Q.S. to pH 5.5 | Q.S. to pH 5.5 |
| Citric Acid | Citric Acid solution | 20 | Q.S. to pH 5.5 | Q.S. to pH 5.5 | Q.S. to pH 5.5 | Q.S. to pH 5.5 | Q.S. to pH 5.5 |
| Water | Purified water, USP | 100 | Q.S. to 100% | Q.S. to 100% | Q.S. to 100% | Q.S. to 100% | Q.S. to 100% |

TABLE 23

| Example | Viscosity (cps) | Foam Volume (ml)* |
|---|---|---|
| E62 | 4149 | 292 |
| E63 | 7241 | 302 |
| E64 | 5245 | 286 |
| E65 | 13960 | 256 |
| C38 | 965 | 227 |

*Tested at 0.1 wt % in simulated hard water.

Composition E66 and Comparative Compositions C39-C40 were made in accord with the following procedure: All materials were added in amounts as indicated for each composition in Tables 24. For example, 3.3% w/w active of Cocamidopropyl Betaine (as given in table 24, C39) corresponds to 8.7% w/w C4, which has an activity of 38% w/w; 3.3% w/w/38% w/w=8.7% w/w.

Composition E66 and Comparative Compositions C39-C40 were made as follows: To an appropriately sized vessel equipped with a hotplate and overhead mechanical stirrer, 90% of the required amount of DI water was added, stirred at 200-350 rpm and heating to 40° C. was started. Glycerin was added and while heating Ucare™ JR400 was added and mixed for 15 mins until completely dispersed. Heating to 80-85° C. was started. While heating, Tween 28 (3.45%) was added to the main batch. At 80-85° C., Ethox™ PEG-6000 was added slowly and mixed until uniform. Cooling to 50-55° C. was started and while cooling, sodium benzoate and Rhodapex™ EST 65 were added. Temperature was kept at 50-55° C. and Tego™ Betaine F50 was added. At or below 40° C., Euxyl™ PE 9010 and Tetrasodium EDTA were added. A premix of the remaining Tween™ 28 and fragrance was made and added to the main batch. The pH was adjusted to 5.1-5.4. Water was added in q.s. to 100 wt %, and the batch is allowed to mix until uniform before being discharged to an appropriate storage vessel. Compositions prepared are listed in Table 24.

The Zero Shear Viscosity and Maximum Foam Volume were measured in accord with the Zero Shear Viscosity Test and Formulation Foam Test, respectively, as described herein. The results are shown in Table 25. As a result, applicants discovered that ZAA surfactants have the tendency to build higher viscosity in comparison to zwitterionic alkylamidoamine hydroxysultaine and betaine surfactants in compositions containing anionic surfactants and several other formulation ingredients, such as PEG-based rheology modifiers, glycerin, fragrance and preservatives. Such compositions also exhibit equivalent or better foamability in comparison to the equivalent compositions containing zwitterionic alkylamidoamine hydroxysultaine and betaine surfactants. Applicants note the comparative examples are normalized to the same surfactant concentrations (% w/w active) as corresponding Inventive Example (C39-C40 correspond to E66).

TABLE 24

| Material | Trade Name | Activity (%) | E66 wt. % | C39 wt. % | C40 wt. % |
|---|---|---|---|---|---|
| E7 | N/A | 31 | 3.3 | | |
| C3 | Mirataine ™ CBS | 42 | | 3.3 | |
| C4 | Tego ™ Betaine F50 | 38 | | | 3.3 |
| PEG-80 Sorbitan Laurate | Tween ™ 28 | 72 | 3.2 | 3.2 | 3.2 |
| PEG-150 Distearate | Ethox ™ PEG 6000 DS | 100 | 1.45 | 1.45 | 1.45 |
| Sodium Trideceth Sulfate | Rhodapex ™ EST-65 | 63.5 | 2.3 | 2.3 | 2.3 |
| Polyquaternium-10 | Ucare ™ JR-400 | 100 | 0.14 | 0.14 | 0.14 |
| Glycerin | Glycerin 99.7 Kosher | 100 | 0.5 | 0.5 | 0.5 |
| Fragrance | Fragrance | 100 | 0.18 | 0.18 | 0.18 |
| Tetrasodium EDTA | Versene ™ 100xl | 100 | 0.5 | 0.5 | 0.5 |
| Sodium Benzoate | Sodium Benzoate, NF, FCC | 100 | 0.3 | 0.3 | 0.3 |
| Phenoxy Ethanol and Ethylhexylglycerin | Euxyl ™ PE 9010 | 100 | 0.7 | 0.7 | 0.7 |
| Sodium Hydroxide | NaOH solution | 32 | Q.S. to pH 5.3 | Q.S. to pH 5.3 | Q.S. to pH 5.3 |
| Citric Acid | Citric Acid solution | 20 | Q.S. to pH 5.3 | Q.S. to pH 5.3 | Q.S. to pH 5.3 |
| Water | Purified water, USP | 100 | Q.S. to 100% | Q.S. to 100% | Q.S. to 100% |

TABLE 25

| Example | Viscosity (cps) | Foam Volume (ml)* |
|---|---|---|
| E66 | 9050 | 100 |
| C39 | 1896 | 82 |
| C40 | 5300 | 80 |

*Tested at 0.1 wt % in simulated hard water.

Composition E67 and Comparative Composition C41 were made in accord with the following procedure: All materials were added in amounts as indicated for each composition in Tables 26. For example, 2.4% w/w active of Cocamidopropyl Betaine (as given in table 26, C41) corresponds to 6.3% w/w C4, which has an activity of 38% w/w; 2.4% w/w/38% w/w=6.3% w/w.

Composition E67 and Comparative Composition C41 were made as follows: To an appropriately sized vessel equipped with a hotplate and overhead mechanical stirrer, 90% of the required amount of DI water was added, stirred at 200-350 rpm and heating to 70-75° C. was started. Sodium benzoate was added and mixed until uniform. While heating, Rhodapex™ ES-2 k was added and mixed until uniform. Then zwitterionic/amphoteric surfactant was added to the main batch and mixed until uniform. Tween™ 28 was added to the main batch and mixed until uniform (at 70-75° C. for at least 10 minutes). Cooling to 40° C. was started. A premix of the Tween™ 20 and the fragrance was made and added to the main batch at or below 40° C. Then Dissolvine™ GL-47-S was added and mixed until uniform. The pH was adjusted to 4.3-5. Dye and sodium chloride solutions were added. Water was added in q.s. to 100 wt %, and the batch is allowed to mix until uniform before being discharged to an appropriate storage vessel. Compositions prepared are listed in Table 26.

The Zero Shear Viscosity and Maximum Foam Volume were measured in accord with the Zero Shear Viscosity Test and Formulation Foam Test, respectively, as described herein. The results are shown in Table 27. As a result, applicants discovered that ZAA surfactants have the tendency to build higher viscosity in comparison to zwitterionic alkylamidoamine betaine surfactants in compositions containing anionic surfactants and several other formulation ingredients, such as PEG-based rheology modifiers, fragrance and preservatives. Such compositions also exhibit equivalent or better foamability in comparison to the equivalent compositions containing zwitterionic alkylamidoamine betaine surfactants. Applicants note the comparative examples are normalized to the same surfactant concentrations (% w/w active) as corresponding Inventive Example (C41 correspond to E67).

TABLE 26

| Material | Trade Name | Activity (%) | E67 wt. % | C41 wt. % |
|---|---|---|---|---|
| E7 | N/A | 31 | 2.4 | |
| C4 | Tego ™ Betaine F50 | 38 | | 2.4 |
| PEG-80 Sorbitan Laurate | Tween ™ 28 | 72 | 0.6 | 0.6 |
| Polysorbate 20 | Tween ™ 20 | 100 | 0.4 | 0.4 |
| Sodium Laureth-2 Sulfate | Rhodapex ™ ES-2K | 26 | 12.2 | 12.2 |
| Fragrance | Fragrance | 100 | 1 | 1 |
| Tetrasodium Glutamate Diacetate | Dissolvine ™ GL-47S | 100 | 0.51 | 0.51 |
| Sodium Benzoate | Sodium Benzoate, NF, FCC | 100 | 0.5 | 0.5 |
| Sodium Chloride | Sodium Chloride 50 | 100 | 1 | 1 |
| Sodium Hydroxide | NaOH solution | 32 | Q.S. to pH 4.5 | Q.S. to pH 4.5 |
| Citric Acid | Citric Acid solution | 20 | Q.S. to pH 4.5 | Q.S. to pH 4.5 |
| Water | Purified water, USP | 100 | Q.S. to 100% | Q.S. to 100% |

TABLE 27

| Example | Viscosity (cps) | Foam Volume (ml)* |
|---|---|---|
| E67 | 9980 | 710 |
| C41 | 3600 | 423 |

*Tested at 0.1 wt % in simulated hard water.

Inventive Example E68 and Comparative Examples C42-C43

Preparation and Mildness Measurement of a Certain Composition of the Invention and Comparative Compositions Composition E68 and comparative Examples C42-C43 had been made according to the process described for C5. Table 28 lists these compositions.

The Zero Shear Viscosity, EpiDerm™ IL-1a concentration and EpiOcular™ $ET_{50}$ were measured in accord with the Zero Shear Viscosity Test, EpiDerm™ Test and EpiOcular™ Test, respectively, as described herein. The results are shown in Table 29. As a result, applicants discovered that ZAA surfactants exhibit similar, if not improved, mildness in comparison to other zwitterionic surfactants like e.g. alkylamidoamine hydroxysultaine and betaine surfactants in compositions containing anionic surfactants.

TABLE 28

| Material | Trade Name | Activity (%) | E68 wt. % | C42 wt. % | C43 wt. % |
|---|---|---|---|---|---|
| E7 | N/A | 31 | 3.75 | | |
| C4 | Tego ™ Betaine F50 | 38 | | 3.75 | |
| C3 | Mirataine ™ CBS | 42 | | | 3.75 |
| Sodium Laureth-2 Sulfate | Rhodapex ™ ES-2K | 26 | 3.75 | 3.75 | 3.75 |
| Sodium Benzoate | Sodium Benzoate, NF, FCC | 100 | 0.50 | 0.50 | 0.50 |
| | Sodium Hydroxide Pellets NF/FCC Grade | 100 | Q.S. to pH 4.5 | Q.S. to pH 4.5 | Q.S. to pH 4.5 |
| Citric Acid | Citric Acid solution | 20 | Q.S. to pH 4.5 | Q.S. to pH 4.5 | Q.S. to pH 4.5 |
| Water | Purified water, USP | 100 | Q.S. to 100% | Q.S. to 100% | Q.S. to 100% |

TABLE 29

| Example | EpiDerm IL-1α (pg/ml) | EpiOcular $ET_{50}$ (h) |
|---|---|---|
| E68 | 175 | 9.9 |
| C42 | 750 | >8 |
| C43 | 373 | not measured |
| $C_{JBS}$ | 215 | not measured under these conditions |

JBS is Johnson's Baby Shampoo—a commercially available benchmark composition.

What is claimed is:

1. A composition comprising a first zwitterionic surfactant comprising 3-((4-coconylamino)-4-oxobutyl)dimethylammonio)-2-hydroxypropane-1-sulfonate;
   and a second surfactant other than said first zwitterionic surfactant, said second surfactant selected from the group consisting of anionic surfactant, cationic surfactant, nonionic surfactant, a zwitterionic surfactant other than the first zwitterionic surfactant, and mixtures thereof; and an ingredient selected from the group consisting of emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliates, pH adjusters, inorganic salts, solvents, viscosity controlling agents and opacifying agents, wherein said composition is substantially free of alkylamidoamine and aminoalkylamine.

2. The composition of claim 1 wherein said composition is free of alkylamidoamine and aminoalkylamine.

3. The composition of claim 1 wherein said composition is substantially free of an anionic surfactant.

4. The composition of claim 1 wherein said composition is substantially free of a sulfated anionic surfactant.

5. The composition of claim 1 comprising from about 0.1% to about 30% of said first zwitterionic surfactant.

6. The composition of claim 1 comprising from about 1% to about 10% of said first zwitterionic surfactant.

7. The composition of claim 3 wherein said first zwitterionic surfactant and said second surfactant are present at a weight ratio of from about 0.003 to about 300.

8. The composition of claim 3 wherein said first zwitterionic surfactant and said second surfactant are present at a weight ratio of from about 0.1 to about 10.

9. The composition of claim 1 having a pH of from about 3 to about 9.

10. The composition of claim 1 comprising from about 0.05 to about 6 weight percent of said inorganic salt.

11. The composition of claim 1 wherein said composition is substantially free of a zwitterionic surfactant comprising an amide moiety.

12. The composition of claim 1 wherein said composition is free of a zwitterionic surfactant comprising an amide moiety.

* * * * *